US010410742B2

United States Patent
Fialkov

(10) Patent No.: US 10,410,742 B2
(45) Date of Patent: *Sep. 10, 2019

(54) METHOD AND SYSTEM FOR INFORMED CONSENT

(71) Applicant: Rational Surgical Solutions, LLC, Des Moines, IA (US)

(72) Inventor: Jonathan Fialkov, Des Moines, IA (US)

(73) Assignee: Rational Surgical Solutions, LLC, Des Moines, IA (US)

( * ) Notice: Subject to any disclaimer, the term of this patent is extended or adjusted under 35 U.S.C. 154(b) by 474 days.

This patent is subject to a terminal disclaimer.

(21) Appl. No.: 14/840,421

(22) Filed: Aug. 31, 2015

(65) Prior Publication Data

US 2016/0110504 A1  Apr. 21, 2016

Related U.S. Application Data

(63) Continuation-in-part of application No. 14/622,978, filed on Feb. 16, 2015.

(Continued)

(51) Int. Cl.
*G16H 10/60* (2018.01)
*G16H 80/00* (2018.01)
(Continued)

(52) U.S. Cl.
CPC .............. *G16H 10/60* (2018.01); *G06F 19/00* (2013.01); *G16H 10/20* (2018.01); *G16H 80/00* (2018.01)

(58) Field of Classification Search
CPC ........ G06Q 50/24; G06Q 50/22; G06Q 10/10; G06Q 10/00; G06Q 20/14; G06Q 10/06;
(Continued)

(56) References Cited

U.S. PATENT DOCUMENTS 3,946,503 A * 3/1976 Buchan .................... G09B 7/08
434/316
6,171,112 B1 * 1/2001 Clark .................... G06Q 50/22
434/322

(Continued)

OTHER PUBLICATIONS

Kulkarni et al, "Audio-video recording of informed consent process:Boon or bane," Perspectives in Clinical Research, Jan.-Mar. 2014 , vol. 5 , Issue 1, pp. 6-10 (Year: 2014).*

(Continued)

*Primary Examiner* — Rachel L. Porter
(74) *Attorney, Agent, or Firm* — McKee, Voorhees & Sease, PLC

(57) ABSTRACT

A method for documenting informed consent includes obtaining a video recording of a patient indicative of informed consent, communicating the video recording across a network for data storage, and storing the video recording in a computer readable data storage medium. The video may include additional portions of a patient encounter. A software application for executing on a computing device may provide a user interface for displaying an educational video to the individual using the software application executing on the computing device, the educational video containing educational content about the procedure for which the informed consent is desired, obtaining video evidencing informed consent for the procedure, administering a quiz to the individual, presenting a document for signature to the individual, receiving a signature for the document from the individual.

4 Claims, 33 Drawing Sheets

Related U.S. Application Data

(60) Provisional application No. 62/065,850, filed on Oct. 20, 2014.

(51) Int. Cl.
*G16H 10/20* (2018.01)
*G06F 19/00* (2018.01)

(58) Field of Classification Search
CPC .. G06Q 10/06395; G06Q 10/20; G06Q 30/02; G06Q 10/06316; G06Q 30/012; G06Q 10/0631; G06Q 10/0633; G06Q 10/0637; G06Q 40/025; G06Q 40/08; G06Q 50/00
USPC .......................................................... 705/2, 3
See application file for complete search history.

(56) References Cited

U.S. PATENT DOCUMENTS

| | | | |
|---|---|---|---|
| 8,190,446 | B2 | 5/2012 | Sobel |
| 8,233,672 | B2* | 7/2012 | Matos ...................... G06K 9/00 340/5.53 |
| 8,655,796 | B2 | 2/2014 | Udani |
| 8,909,811 | B2 | 12/2014 | Margolis et al. |
| 2006/0282292 | A1 | 12/2006 | Brink et al. |
| 2010/0017231 | A1* | 1/2010 | Galbraith .............. G06F 19/327 705/3 |
| 2010/0092937 | A1 | 4/2010 | Jackson |
| 2012/0035949 | A1 | 2/2012 | Brink et al. |
| 2012/0127157 | A1 | 5/2012 | Adler et al. |
| 2012/0310670 | A1 | 12/2012 | Pruitt |
| 2013/0019149 | A1 | 1/2013 | Spencer et al. |
| 2013/0135160 | A1* | 5/2013 | Dixon ..................... H01Q 1/44 343/720 |
| 2013/0149683 | A1* | 6/2013 | Steerman ............... G09B 19/00 434/236 |
| 2014/0141397 | A1 | 5/2014 | Dunn |
| 2014/0187888 | A1* | 7/2014 | Hatziantoniou ....... A61B 5/747 600/365 |
| 2015/0046174 | A1 | 2/2015 | Mainwaring et al. |
| 2015/0248230 | A1* | 9/2015 | Mark ..................... H04L 67/10 715/747 |
| 2015/0261918 | A1* | 9/2015 | Thornbury, Jr. ........ G06Q 50/24 705/3 |

OTHER PUBLICATIONS

"The Patient Education Materials Assessment Tool (PEMAT) and User's Guide", http://www.ahrq.gov/sites/default/files/publications/files/pemat-av.pdf, available online Aug. 19, 2015.

* cited by examiner

Quiz Results — 202

< Quiz — 204

What operation did Dr. Fialkov discuss with you today? — 146
Correct Answer: Radical Prostatectomy with Lymph Node Dissection (removal of prostate and lymph nodes for prostate cancer) — 156

What is NOT a potential problem that can arise from this operation — 162
Correct Answer: Weight gain — 166

What is the approximate cancer cure rate for this operation given your pathology report from the recent biopsy Dr. Fialkov performed? — 172
Selection: 0% — 176
Correct Answer: 80% — 178

Dr. Fialkov will perform this procedure with the DaVinci Robot but will make a full-sized incision in the lower abdomen (belly) if he encounters any unexpected challenges during the surgery. True or False? — 182
Correct Answer: True — 186

What problems can arise after this surgery once you get home? — 192
Selection: Pneumonia — 196
Correct Answer: All of the above — 198

Finish

*FIG. 19*

Consent for Surgery or Procedure

- Please read the form.
- Ask about any part you do not understand.
- Be sure you have your questions answered before you sign this form.
- When you sign it, you are giving us permission to do this surgery or procedure.

I, Anthony Wallace _____ (patient's name) agree for Dr _____
along with any assistants the doctor may choose, to do this surgery or procedure on
me at: _____
Name of licensed facility
Radical Retropubic Prostatectomy with Pelvic Lymph Node Dissection
_____

Name of surgery or procedure in medical words—including left, right, or level
(Doctor or health care worker fills this out)
_____

Name of surgery or name of procedure in my own words
(What the patient or family says back to the doctor or health care worker-quote
patient or family)

1. I understand that my doctor may find other medical conditions he/she did not expect during my surgery or procedure. I agree that my doctor may do any extra treatments or procedures he/she thinks are needed for medical reasons during my surgery or procedure.
2. I understand I may be given medicine to put me to sleep, make parts of my body numb, or help control pain. People with special training will give this medicine. These people may be an anesthesiologist, a nurse anesthetist (CRNA), a nurse, or the doctor doing my surgery or procedure.
3. I understand the doctor may remove tissue or body parts during this surgery or procedure. If it is not used for lab studies or teaching, it will be disposed of, as the law requires.
4. I understand I may be given a substance during an x-ray, if needed, so the tissue in my body can be better seen on the exam.
5. I understand pictures or video of my surgery or procedure may be taken, if my doctor thinks it is needed for medical reasons.
6. I understand someone may watch or help with my surgery or procedure for medical teaching. These people are usually medical or nursing students. A technical advisor may watch if my doctor thinks one is needed.
7. I understand that if my doctor thinks I need blood for medical reasons, it will be given.

METHOD AND SYSTEM FOR INFORMED CONSENT

CROSS REFERENCE TO RELATED APPLICATIONS

This is a Continuation-in-part application of U.S. Ser. No. 14/622,978 filed Feb. 16, 2015, which claims priority under 35 U.S.C. § 119 to provisional application U.S. Ser. No. 62/065,850 filed Oct. 20, 2014, all of which are herein incorporated by reference in their entirety.

FIELD OF THE INVENTION

The present invention relates to technology for obtaining and retaining records of informed consent.

BACKGROUND OF THE ART

Although the present invention has uses in various areas, the background of the invention is discussed with respect to particular problems in the medical profession. The invention is not, however, necessarily limited to these particular medical applications.

In medicine, informed consent is important. Generally informed consent involves health care providers providing complete information about the nature of a medical procedure or other event. This information can include information about possible complications, who is performing the procedure, and other relevant information which may vary depending on the circumstances. The patient needs to understand what is being conveyed and be competent to make a decision in view of the information provided by the health care provider. This process is consistent with medical ethics.

Informed consent is generally obtained by having the patient sign a document indicating that they have provided their informed consent after they have had a discussion with their health care provider and/or reviewed appropriate written materials. This step is helpful for legal reasons as the patient contractually agrees that they have given their informed consent. Failure to obtain consent can result in claims of battery, negligence, or other legal claims against a health care provider regardless of whether medical procedures were performed competently. Despite written consent, problems remain.

For example, patients may fail to recall conversations with the health care provider and informed consent documents may not always capture all information discussed between patients and health care providers or establish that patients had the opportunity to have all of their questions and concerns addressed. What is needed is a technological solution which improves the informed consent process.

SUMMARY

Therefore, it is a primary object, feature, or advantage of the present invention to improve over the art.

It is a further object, feature, or advantage of the present invention to obtain informed consent from patients in a manner consistent with the highest order of medical ethics.

It is a still further object, feature, or advantage of the present invention to improve the communications between health care provider and patient in situations where informed consent is needed.

Another object, feature, or advantage of the present invention is to improve upon the documentation of informed consent.

Yet another object, feature, or advantage of the present invention is to eliminate or defend against frivolous claims for failure to obtain informed consent.

Another object, feature, or advantage is to provide a method of obtaining informed consent which can be used in different industries.

Yet another object, feature, or advantage is to provide a software application with the ornamental design as shown.

A further object, feature, or advantage is to provide the ability for health care providers to choose videos from a library of videos for use in providing their patients with informed consent.

A further object, feature, or advantage is to provide the ability for patients and health care providers to be in separated locations, including remote from one another, and obtain informed consent from patients.

A further object, feature, or advantage is to provide an integrated system for informed consent or analogous consent including health care related events as well as others.

A further object, feature, or advantage is to provide verification of understanding of instructional and educational content used in the informed consent process with high level of competence and documenting the same.

A further object, feature, or advantage is to provide informed consent, techniques across the range of times, events, or milestones in a process in need of informed consent. In one example, it could be at a pre-event time (in a medical context pre-operation counseling session), it could be prior to an event (in the medical context prior to surgery or a medical procedure), and/or at a subsequent event (in a medical context, a post-operative counseling event). Ancillary features such as communication via text messages and emails, providing links to a web based set of content, and use of other automatic documenting, milestone data (e.g., time stamps, GPS location), are possible in an integrated system.

One or more of these and/or other objects, features, or advantages of the present invention will become apparent from the specification and claims that follow. No single embodiment need exhibit each and every object, feature, or advantage and different embodiments may have different objects, features, or advantages.

According to one aspect, a method for documenting informed consent is provided. The method includes obtaining a video recording of a patient indicative of informed consent, communicating the video recording across a network for data storage, and storing the video recording in a computer readable data storage medium. The method may further include positioning at least one video camera in a room associated with a health care provider in which the patient provides the informed consent. The method may further include retrieving the video recording of the patient indicative of informed consent over the network and from the computer readable storage medium. The method may further include providing a user interface to the health care provider for accessing the video recording. The method may further include combining data from a health care information system with the video recording. The video recording may further include at least a portion of a patient encounter. The method may further include making the video recording available to the patient through a portal. The method may further include making the video available to the patient by placing the video on a USB drive.

According to another aspect, a method for obtaining and documenting informed consent is provided. The method includes providing a software application to a computing device for executing on the computing device, receiving a selection of an individual into the software application executing on the computing device. The method may further include receiving a selection of a procedure for which informed consent is desired into the software application executing on the computing device. The method may further include displaying an educational video to the individual using the software application executing on the computing device, the educational video containing educational content about the procedure for which the informed consent is desired. The method may further include the patient and health care provider and/or agent of the health care provider (being in different and even remote locations, each having a computing device with application and video capture device, for example a web cam), and communicating, recording, and storing activities related to obtaining patient informed consent. The video telephony, including but not limited to using peer-to-peer, N2N encrypted, video chat technology. The method may further include capturing video evidencing informed consent for the procedure using the software application executing on the computing device and making available a quiz for the individual using the software application executing on the computing device, the quiz including a plurality of questions about the procedure for assessing informed consent. The method may further include documenting administration of the quiz to the individual using the software application executing on the computing device, presenting a document for signature to the individual using the software application executing on the computing device, the documenting indicative of informed consent for the procedure. The method may further include receiving a signature on the document from the individual using the software application executing on the computing device, and sending to a server from the computing device the video, the document with the signature, and storing the video in a non-transitory computer readable data storage medium associated with the server to thereby provide for documenting the informed consent of the individual for the procedure.

The capturing of video may be performed using a camera integrated into the computing device. The method may further include receiving a selection of an option to bypass the quiz and documenting a reason for bypassing the quiz by sending the reason to the server. The procedure may be a medical procedure and the individual may be a patient. The video may include video of the patient acknowledging that they are providing informed consent. The method may further include making the video available to the individual through a portal associated with the server. The method also may further include making the video available to a service provider of the individual through a portal associated with the server. The video may include video of the individual and a service provider interacting with the individual. The method may further include receiving through the software application setting information identifying a plurality of procedures and one or more procedure types. The method may further include receiving through the software application the document associated with the procedure. The method may further include receiving through the software application the plurality of questions about the procedure. The software application may be a mobile app and the computing device may be a mobile computing device.

According to another aspect, a method for obtaining and documenting informed consent for a procedure from an individual is provided. The method includes providing a software application to a computing device for executing on the computing device wherein the software application provides a user interface for obtaining video evidencing informed consent for the procedure, administering a quiz to the individual, presenting a document for signature to the individual, receiving a signature for the document from the individual. The method further includes receiving a selection of a procedure for which informed consent is desired into the software application executing on the computing device. The method may further include displaying an educational video to the individual using the software application executing on the computing device, the educational video containing educational content about the procedure for which the informed consent is desired. The method may further include capturing the video evidencing informed consent for the procedure using the software application executing on the computing device, and presenting the document for signature to the individual using the software application executing on the computing device, the documenting indicative of informed consent for the procedure. The method may further include receiving the signature on the document from the individual using the software application executing on the computing device and sending to a server from the computing device the video, the document with the signature, and storing the video in a non-transitory computer readable data storage medium associated with the server to thereby provide for documenting the informed consent of the individual for the procedure. The method may further include administering the quiz for the individual using the software application executing on the computing device, the quiz including a plurality of questions about the procedure for assessing informed consent. The method may further include documenting administration of the quiz to the individual using the software application executing on the computing device and sending a record of the administration of the quiz to the server from the computing device.

According to another aspect, a system is provided for obtaining and documenting informed consent. The system may include a software application for executing on a computing device wherein the software application provides a user interface for obtaining video evidencing informed consent for the procedure, administering a quiz to the individual, presenting a document for signature to the individual, receiving a signature for the document from the individual.

BRIEF DESCRIPTION OF THE DRAWINGS

FIG. 19 is a screen display for a mobile app showing an example of quiz results.

FIG. 21 is a screen display showing a mobile app with a consent for surgery or procedure document.

FIG. 23 is a screen display showing a mobile app with a signed consent document.

DETAILED DESCRIPTION

The present invention provides for a comprehensive system and related methods for obtaining informed consent including video records of informed consent. Primarily, the invention will be described with respect to a software application suitable for use on a mobile computing device which may be referred to as a "mobile app." It is to be understood, however, that the software application described may execute on any number of different types of computing devices including desktop computers, notebook computers, tablets, wearable computers, phones, or other types of computing devices. The computing device may use any number of different types of operating systems including iOS, Android, Blackberry, Windows, or other operating systems. The software may be written in any number of different types of languages using any number of different types of platforms or tools. As shown herein the mobile app is executing on an Apple iPAD with an iOS operating system which provides a touch screen interface. The Apple iPAD also includes multiple video cameras.

Figure 1A:
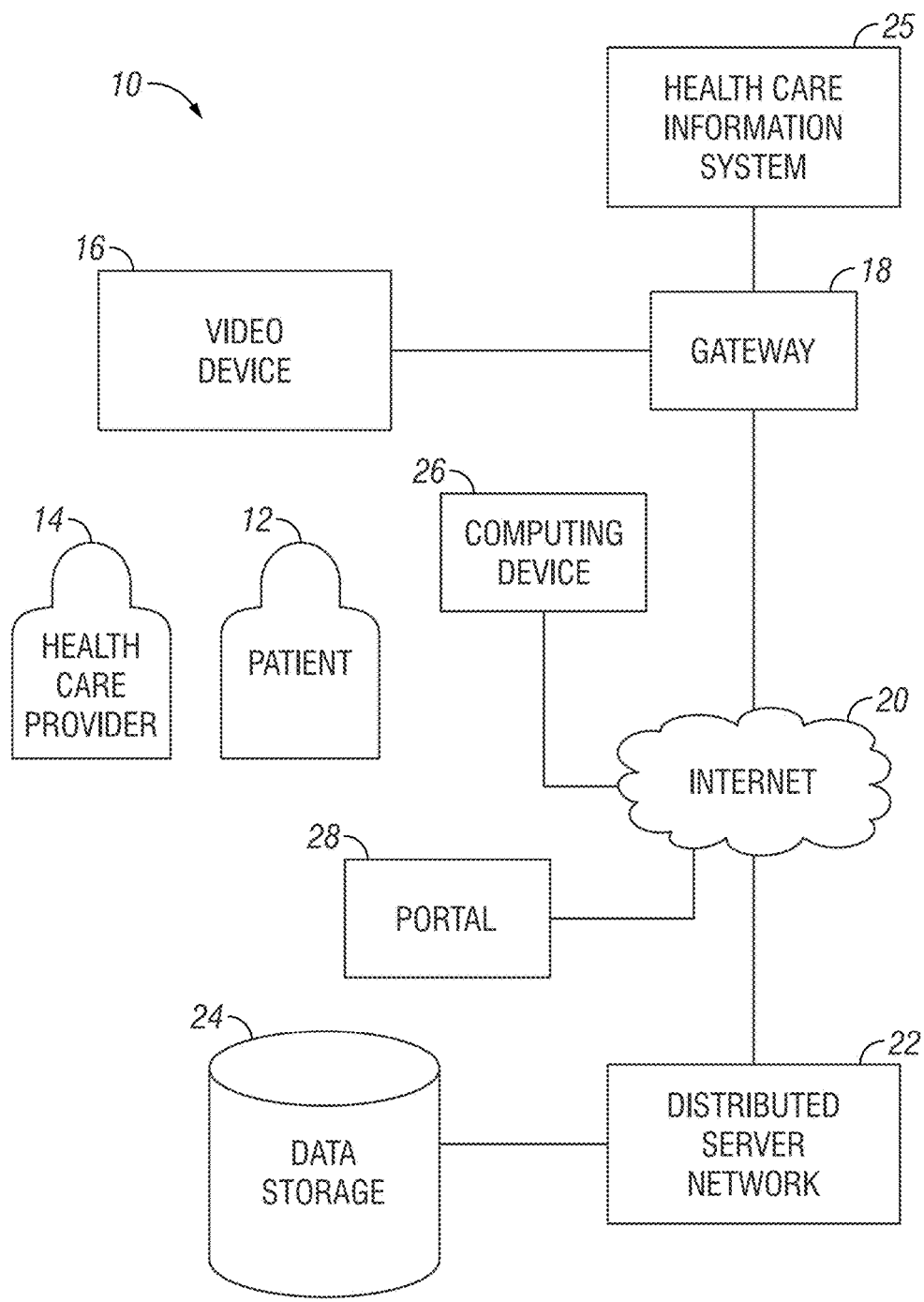
FIG. 1A is a diagram illustrating one example of a system for obtaining informed consent using video.

FIG. 1A illustrates a system 10. A patient 12 and health care provider 14 are shown. A video device 16 is shown which may be used to acquire audio and video of the patient 12 and/or interactions between the patient 12 and the health care provider 14. The video device 12 may include one or more cameras or other imaging devices located in a patient examination room, office, or other location in a physician's office or other health care facility.

One or more video devices 16 may be operatively connected to a gateway 18. The gateway 18 may be operatively connected to the internet 20. The internet may be operatively connected to or include a distributed server network 22. The distributed server network 22 may be operatively connected to data storage 24.

In addition, it is also contemplated that one or more health care information systems 25 associated with the practice of the health care provider may also be operatively connected to the gateway 18. It is contemplated that information from the health care information system 25 may be combined with the video either automatically or manually to identify the video such as with a unique patient identifier, type of procedure for which informed consent is given, or other information. In addition, stored videos may be made available to the health care information system 25.

In operation, a health care provider 14 may discuss with a patient 12 an upcoming medical procedure, the attendant risks, who will be performing the procedure, possible complications, and other relevant information. The patient 12 may ask questions that they have about the procedure, confirm that they have read appropriate literature and verify that they are giving consent. The patient may then sign a written document confirming that they have provided informed consent or electronically sign a document confirming that they are providing informed consent. During this, or any other interaction, the video device 16 may record relevant audio and video. Thus, a record of all or a part of the interaction may be recorded. For example, the portion of the interaction where the client signs the informed consent may be recorded. The patient may be asked to read a statement confirming their consent on the video. The video may then be communicated through the gateway 18 and the internet 20, over a distributed server network 22 and to data storage 24. The video may then be made available to a computing device 26 for playback by the health care provider 14. In some embodiments, the video may also be made available to the patient 12. The video may be made available to the patient 12 through a web site portal, mobile app, or other portal 28. Alternatively, the video may be available to the patient by storing the video for the patient on a computer readable storage medium such as a USB drive. The communication and storage of the video are performed securely in a manner consistent with all applicable health privacy laws and regulations.

As described, the method and system provides for a number of different advantages. First, there is a more complete record of the informed consent. Patients are more apt to remember the interaction leading up to the informed consent when acknowledgement of the informed consent is made for video archive purposes. Patients are also more likely to appreciate the importance of the informed consent when (in their view) the process involves more than merely a form to sign but a video recorded confirmation of their consent. In addition, the video would provide additional evidence in legal proceedings which would be highly relevant to the legal determination of whether informed consent was provided or not.

In situations where all or a portion of the interaction between the health care provider and patient is recorded an additional record of the complete interaction between health care provider and patient is made. Another potential benefit is that this may potentially be shared with the patient for their records in case they want to review information conveyed to them before their procedure. This information may be shared through a web site portal, through a mobile app, or may be stored on a computer readable storage medium such as a USB drive.

Where all or a portion of the interaction between the health care provider and the patient is recorded this may also be advantageous in showing the patient that the health care provider is being very transparent in their communications and that informed consent is being provided in an appropriate manner.

Figure 1B:
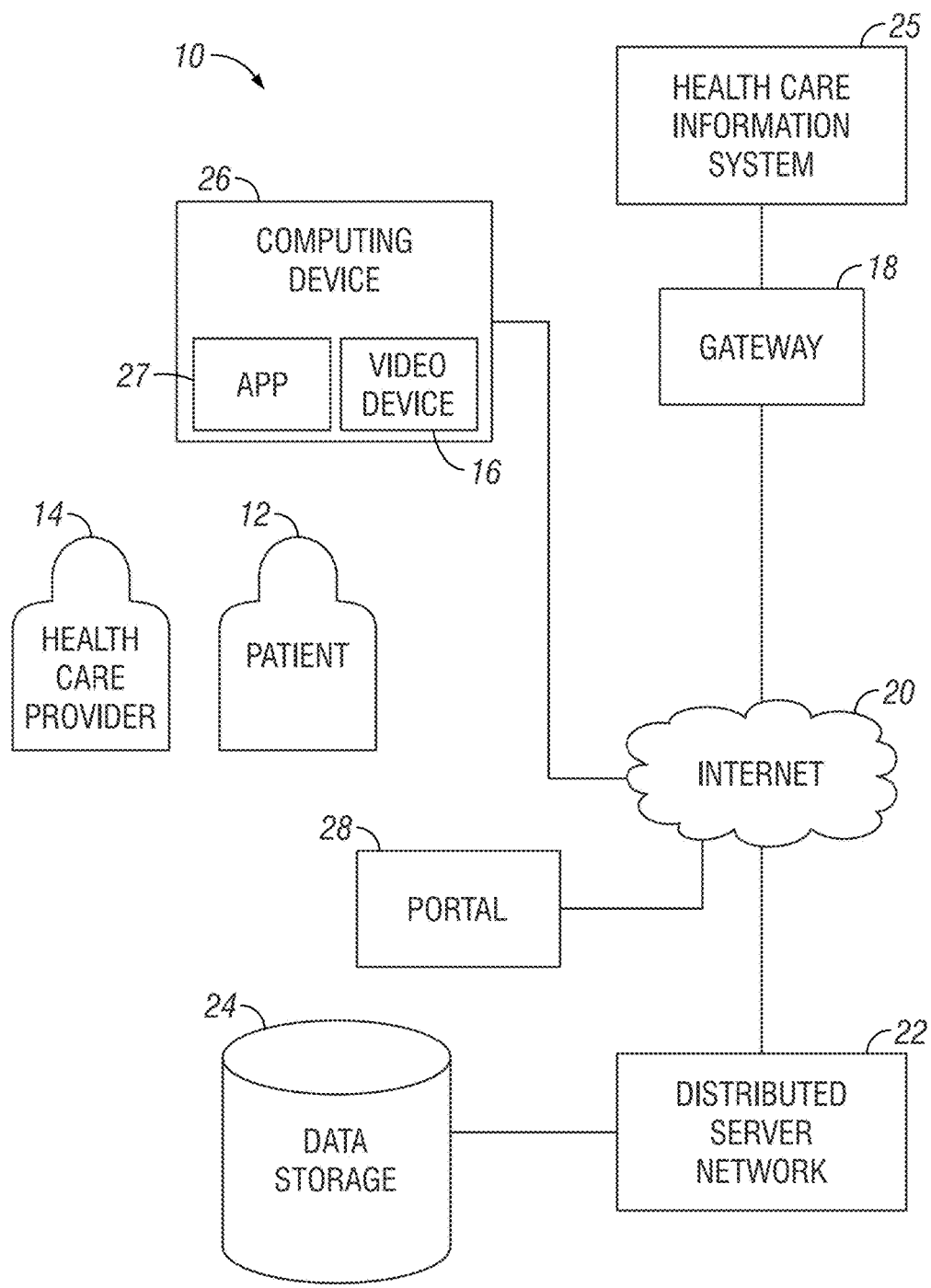
FIG. 1B is another diagram illustrating another example of a system for obtaining informed consent using video.

As previously discussed, in one embodiment the video camera may be mounted or otherwise positioned in a patient examination room or other room. Alternatively, a video camera associated with a mobile device or other computing device such as a tablet computer may be used to record the informed consent. Where used, the video may be wirelessly communicated to the gateway 18 shown in FIG. 1A.

Where a mobile device is used, any documents pertaining to informed consent may be signed in addition to video being recorded. FIG. 1B illustrates an embodiment with a computing device 26 which includes a non-transitory computer readable memory for storing an app 27. One or more cameras or other imaging devices 16 may be a part of the computing device 26. The computing device 26 may, for example, be a mobile device such as a tablet computer.

Although a health care provider 14 and a patient 12 are shown it is to be understood that the health care provider is one example of a service provider and the patient may be a customer or client. In addition, the health care information system 25 may be another type of information system associated with a different type of business.

Figure 1C:
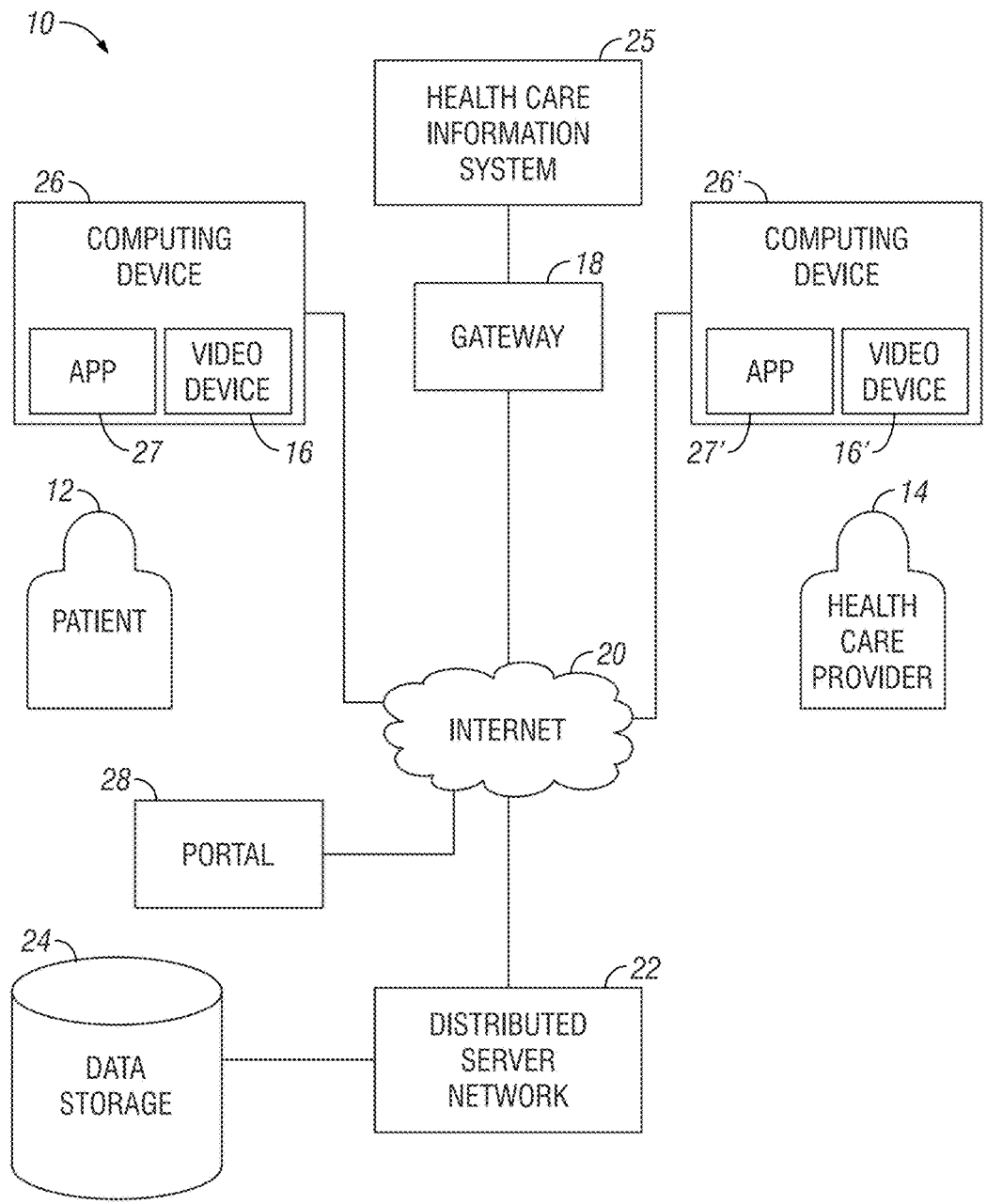
FIG. 1C is another diagram illustrating another example of this system through obtaining informed consent using video telephony.

FIG. 1C illustrates another example of a system that can use at least some aspects of the present invention. Patient 12 and health care provider 14 (or a representative of the same) can be in separate or geographically remote locations. Each would have a computing device (for patient 12 computing device 26; for health care provider 14 computing device 26'). Utilizing video telephony, patient 12 and health care provider personnel 14 can communicate via both sight and sound (video and audio). In one example, a Skype® Brand application can be installed on each computing device 26 and 26 prime. Such applications are available for any computing device that is internet-enabled, including mobile devices and smart phones. Such applications can include security features such as user authentication and N2N encryption. Instead of the health care provider 14 and the patient 12 being in the same room and being able to have face to face view and communication, this would allow remote video and audio teleconferencing type communication. By appropriate technology, at least a portion of any captured video and audio from video device 16 or 16' can be captured and stored to document events involved in obtaining informed consent from patient 12. For examples of utilizing video telephony, such as Skype®, reference can be taken to U.S. Pat. No. 8,533,611 and published in U.S. Publication 2013/0117395, both incorporated by reference herein. Essentially it is the same process as in the doctor's or health care provider's office, as discussed elsewhere herein, but the doctor communicates to the patient through video conference. The system allows recording, encrypting, compressing, and/or storing on a server at least a part of the video conference. The application enabling the same can be to a stand-alone website, or using an existing telemedicine interface.

Additional applications may have to be used to allow recording of the teleconference. For example, Skype® does not natively support call recording. However, its website lists applications that can be used in both Windows and Mac devices that allow recording of Skype® calls. Examples are listed at http://support.skype.com/ EN/fax/FA12395/how-can-I-record-my-skype-calls. Software of the computing device can then capture link, and transmit any of the recorded teleconference in correlation to the informed consent process to a remote server. See for example U.S. Pat. No. 8,909,811 and US 2013/0019149 for examples of recording such things as peer-to-peer telephony recording, both incorporated by reference herein.

Figure 2:
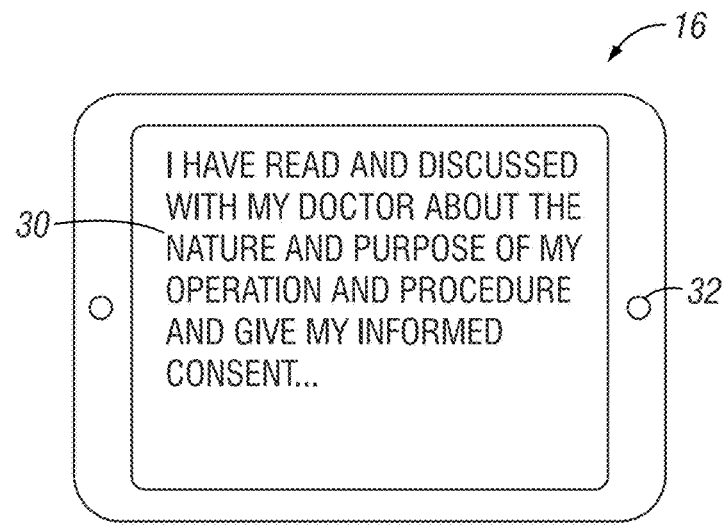
FIG. 2 is a diagram of a screen display of a user interface for a patient to review informed consent documentation.

FIG. 2 illustrates an example of a mobile device 16 with a display 30 and a camera 32. In one embodiment, the patient may be asked to read a statement re-affirming their informed consent while on camera.

Figure 3:
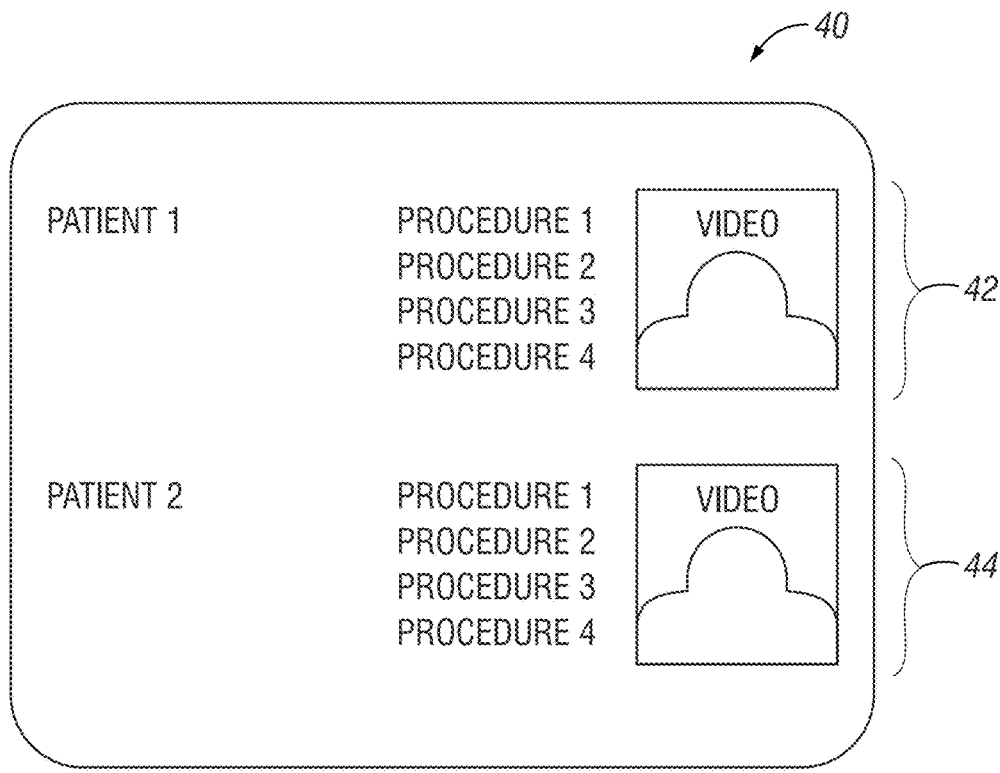
FIG. 3 is a screen display of a user interface for a health care provider to review informed consent videos.

Once the informed consent videos are stored they may be accessed as needed. FIG. 3 is an example of a screen display 40 illustrating that for each patient there may be one or more examples of informed consent they have given on different occasions and corresponding video is also made available. Thus as shown, for a first patient there are multiple procedures and videos 42 listed and also for a second patient there are multiple procedures and videos 44 listed. Thus, the health care provider has a record of the informed consent.

Figure 4:
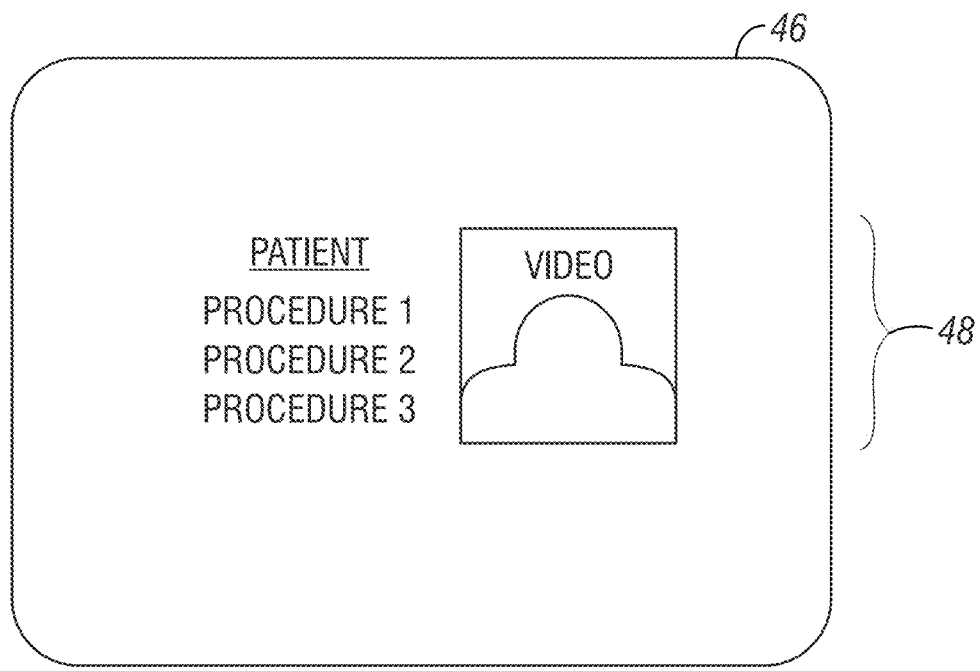
FIG. 4 is a screen display of a user interface for a patient to review informed consent videos.

FIG. 4 illustrates one example of a portal 46 where a patient may view examples of informed consent 48 which they have previously given. Thus, after a visit with a health care provider, a patient can go back and review informed consent videos if they would like. Alternatively, the informed consent video may be stored on a computer readable storage media such as USB drives and given to the patient at the time of the visit.

Figure 5:
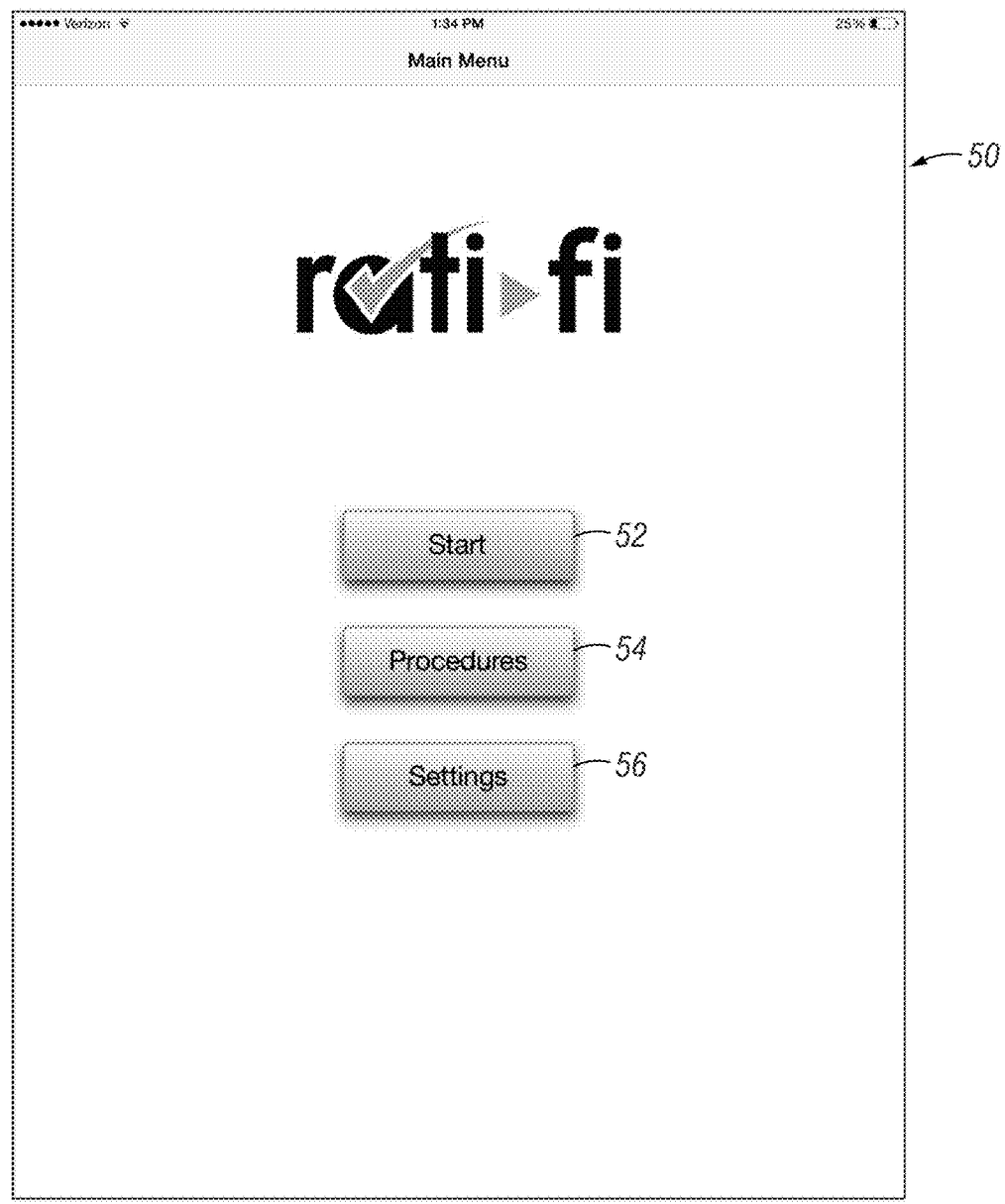
FIG. 5 is a screen display from a mobile app for obtaining informed consent.

FIG. 5 is a screen display 50 from a mobile app for obtaining informed consent. As shown on a "Main Menu", there is a "Start" button 52, a "Procedures" button 54, and a "Settings" button 56. The mobile app may be operated by a health care provider in order to obtain informed consent from patients.

Figure 6:
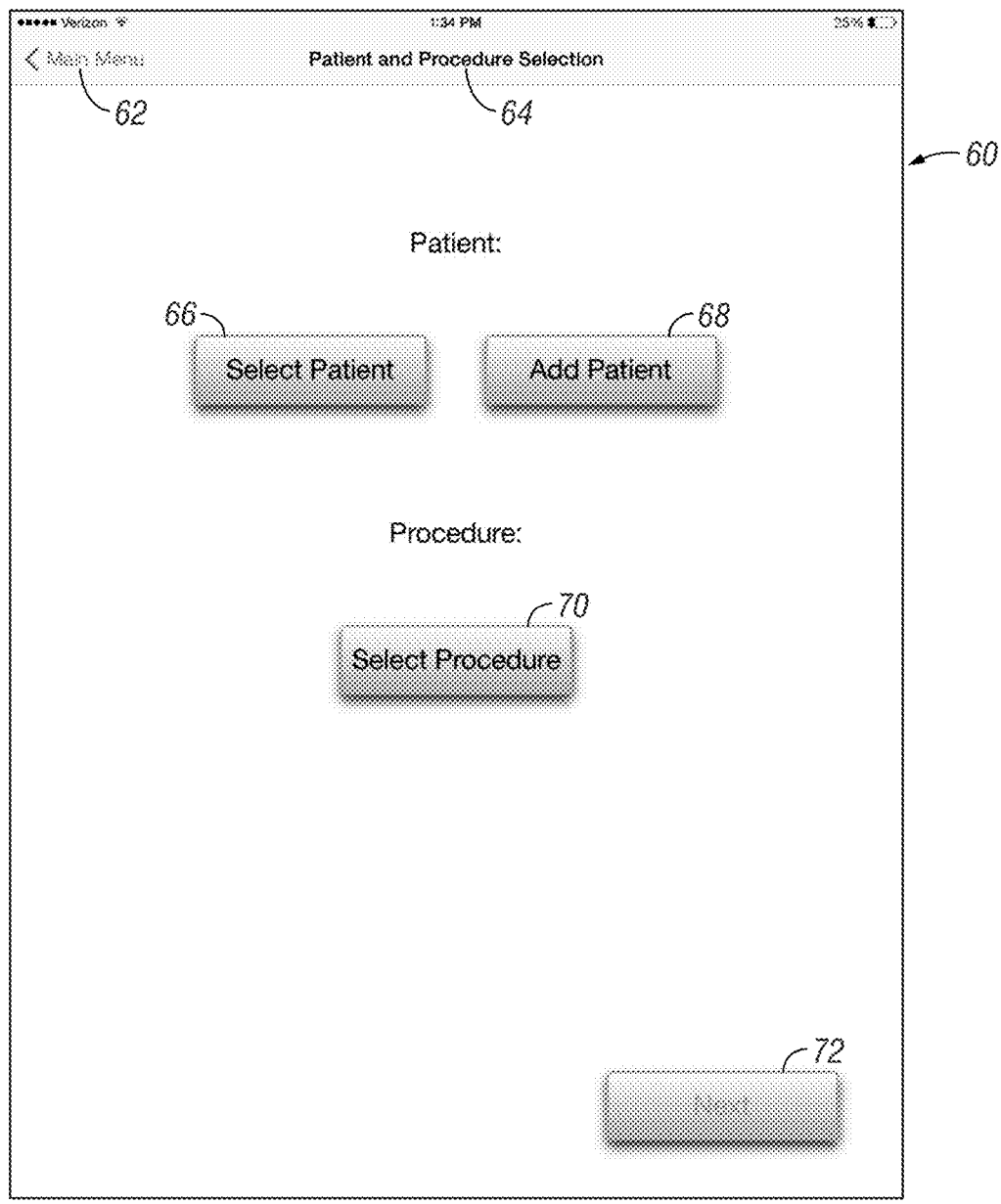
FIG. 6 is a screen display for a mobile app allowing a user to select a patient, add a patient, or select a procedure.

FIG. 6 is a screen display 60 for a mobile app allowing a user to select a patient using a "Select Patient" button 66, add a patient using an "Add Patient" button, or select a procedure using a "Select Procedure" button. The screen is identified as a "Patient and Procedure Selection" screen 64. A user can navigate back to the "Main Menu" 62. Once appropriate patient and procedure selections have been made a user can advance by selecting the "Next" button 72. The "Next" button 72 may be disabled unless and until the patient and procedure selections have been made.

Figure 7:
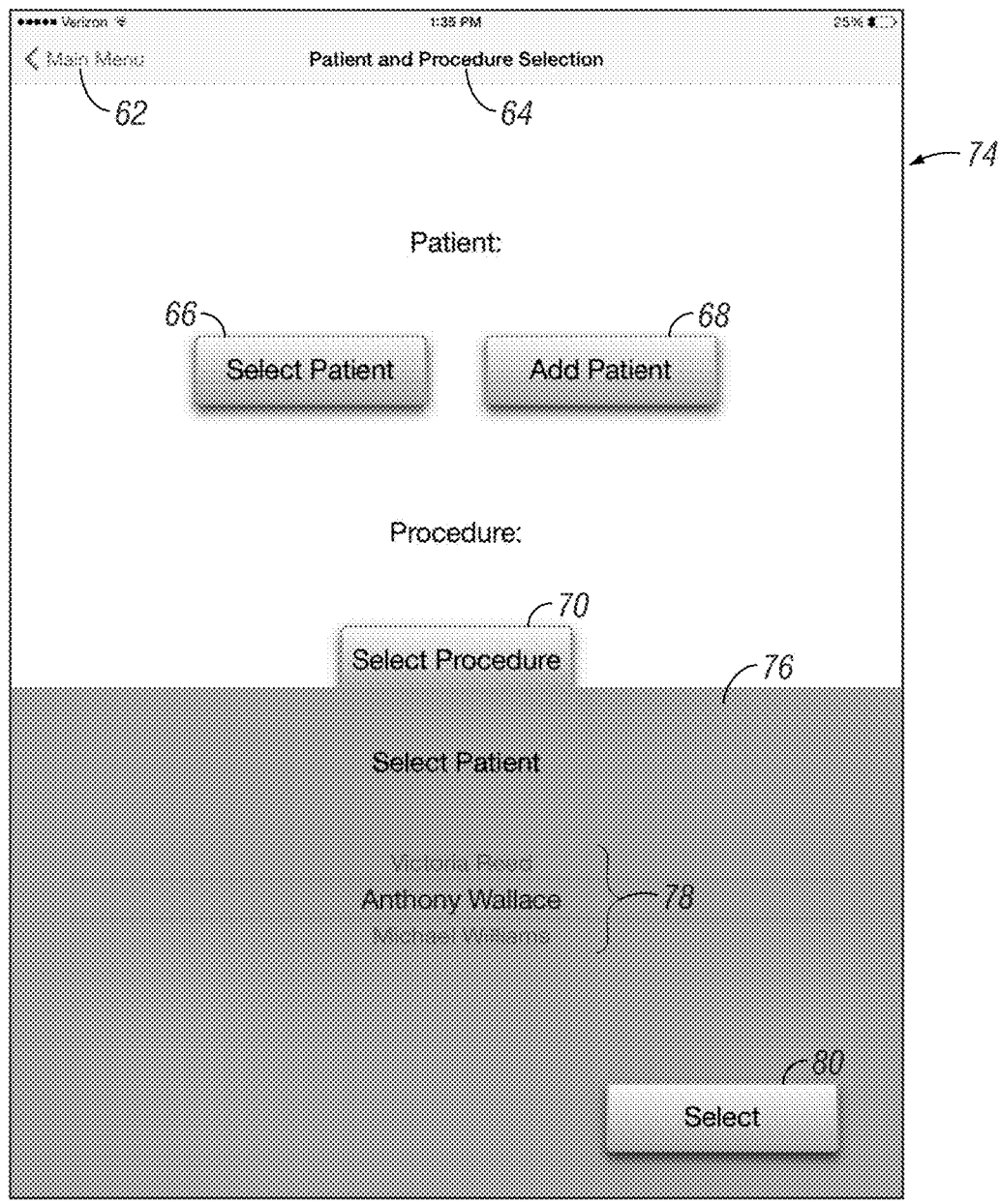
FIG. 7 is a screen display for a mobile app for obtaining informed consent where a user is permitted to select a patient.

FIG. 7 is a screen display 74 for a mobile app for obtaining informed consent where a user is permitted to select a patient. A "Select Patient" window 76 is shown which allows a user to select a patient from a list of patients 78 and confirm this selection by using the "Select" button 80.

Figure 8:
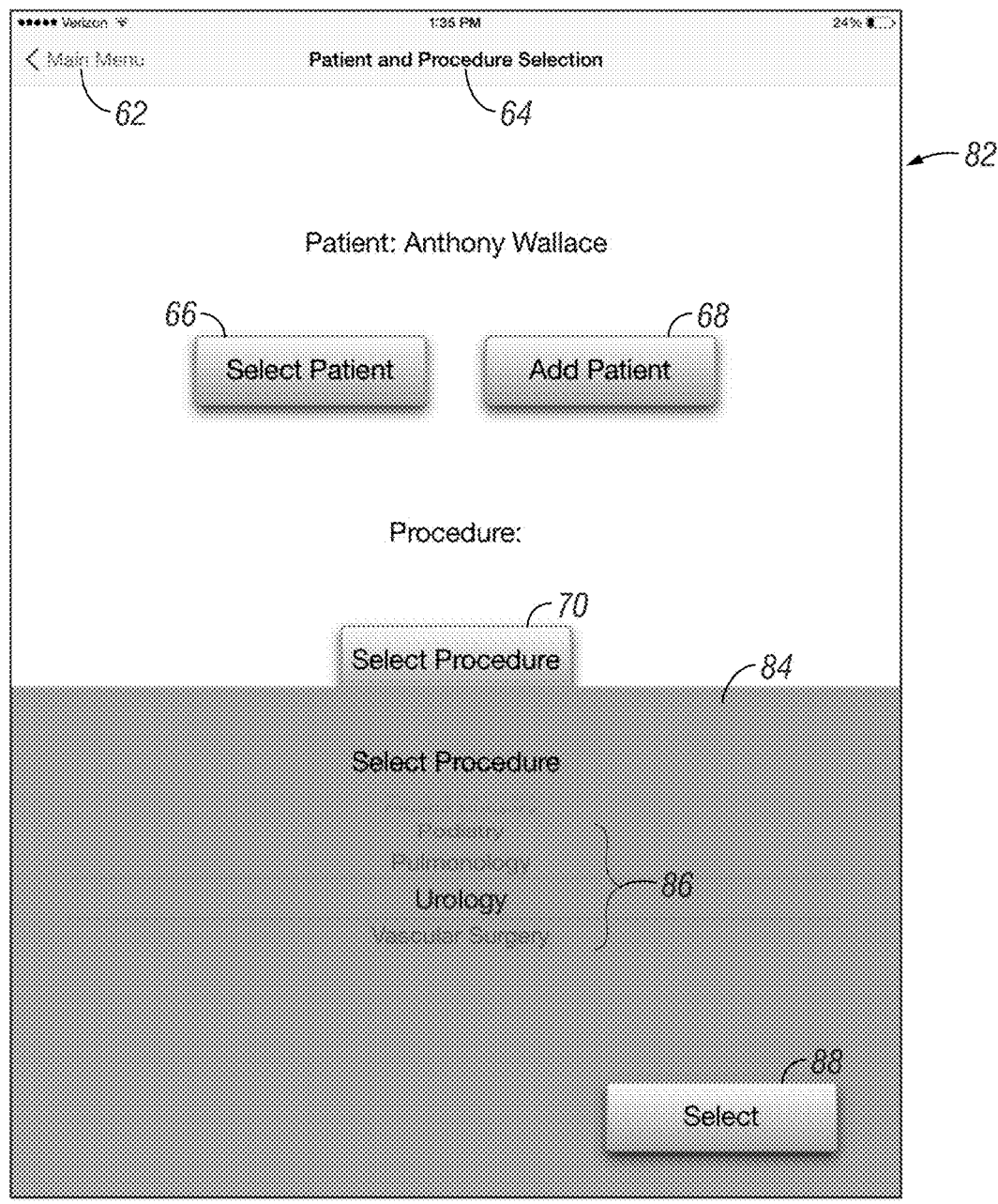
FIG. 8 is a screen display for a mobile app for obtaining informed consent where a user is permitted to select a procedure.

FIG. 8 is a screen display 82 for a mobile app for obtaining informed consent where a user is permitted to select a procedure. Note that the user has already selected a patient. A "Select Procedure" window 84 is shown which allows a user to select a procedure from a list of procedures 86 and confirm this selection by using the "Select" button 88.

Figure 9:
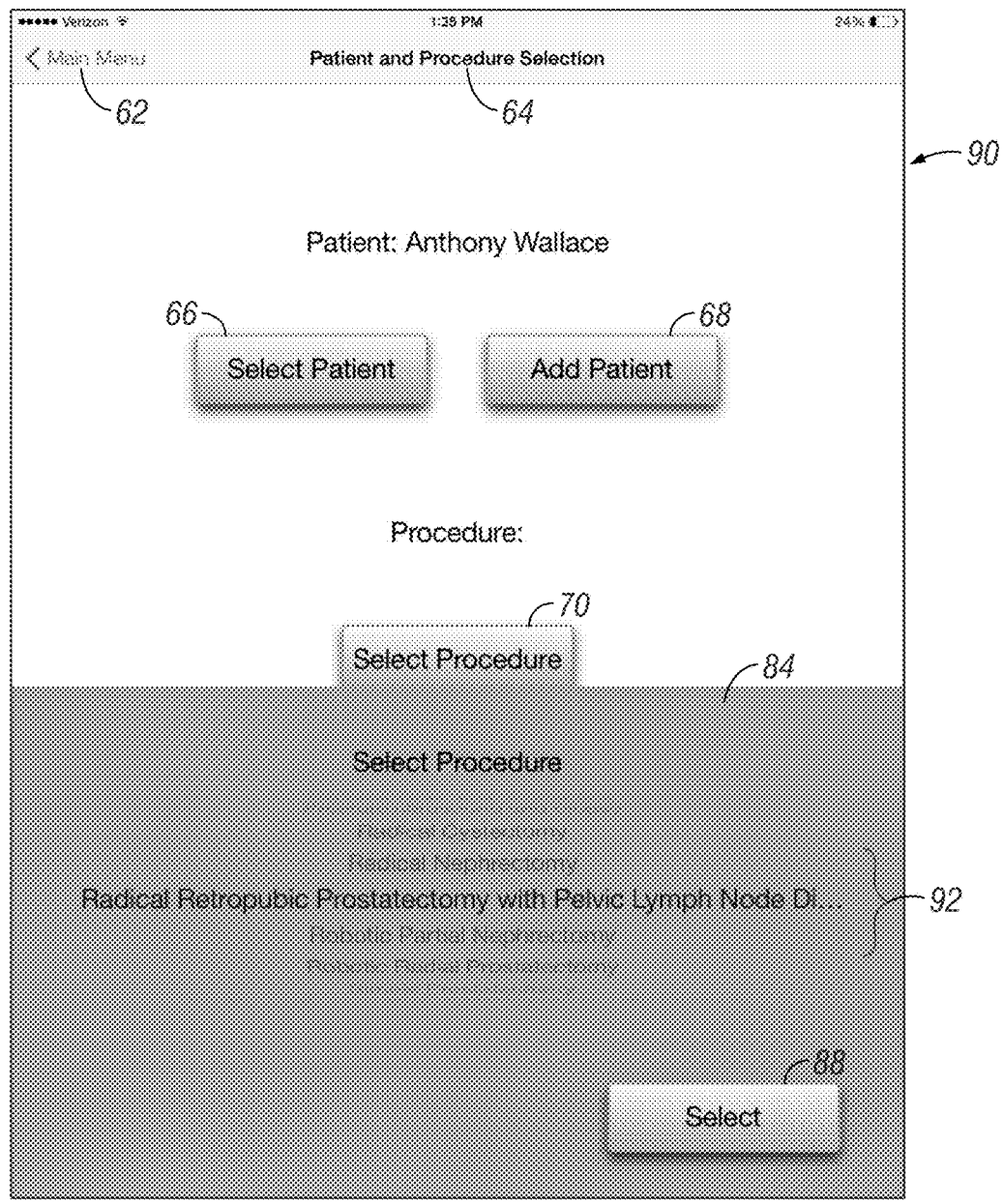
FIG. 9 is another screen display for a mobile app for obtaining informed consent where a user is permitted to select a procedure.

FIG. 9 is another screen display 90 for a mobile app for obtaining informed consent where a user is permitted to select a procedure. FIG. 9 is similar to FIG. 8, however a different procedure within the list of procedures 92 is selected, in this case a Radical Retropubic Prostatectomy with Pelvic Lymph Node Dissection.

Figure 10:
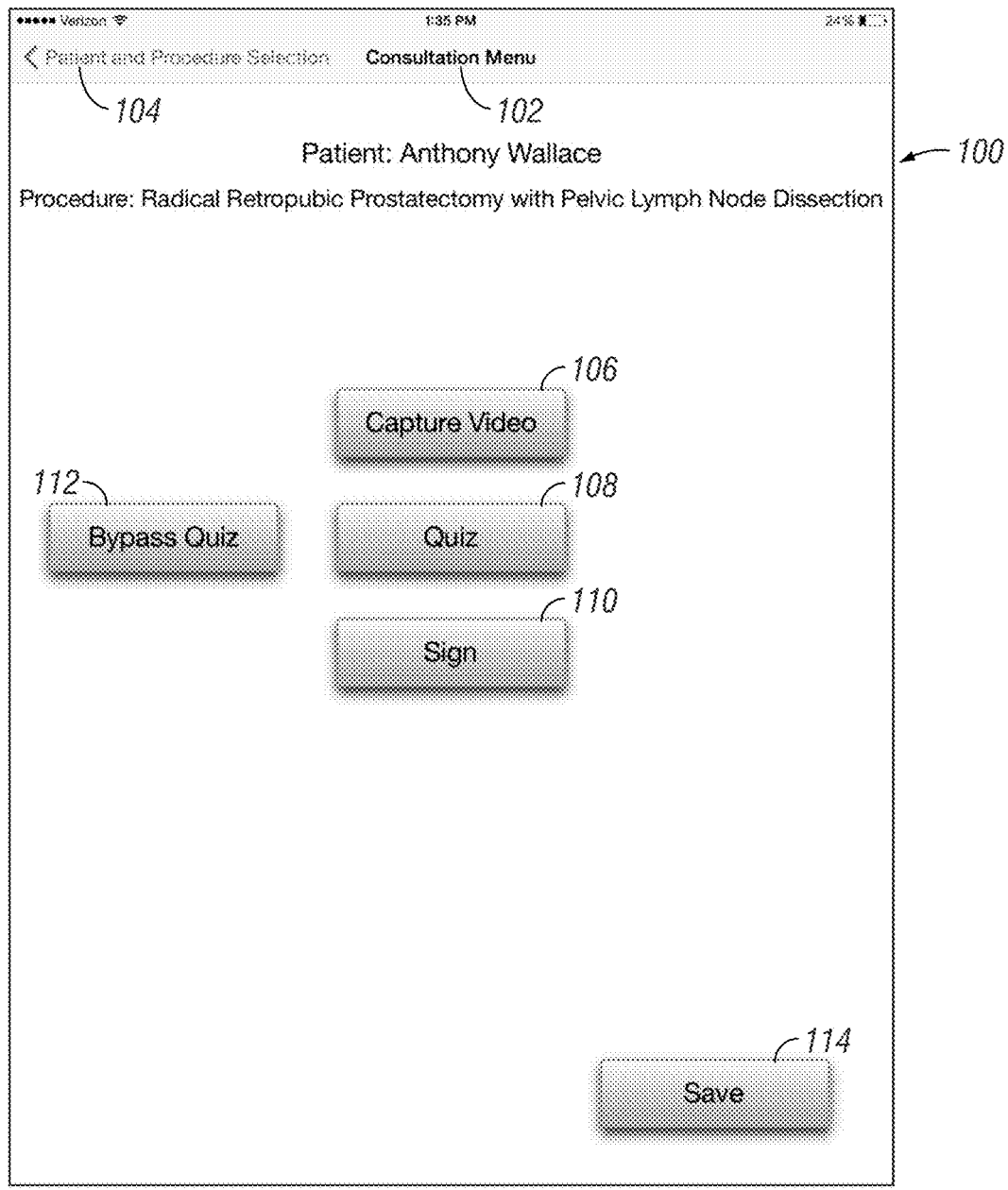
FIG. 10 is a screen display for a mobile app which includes a consultation menu.

FIG. 10 is a screen display 100 for a mobile app which includes a consultation menu 102. The user may select to return to the Procedure Selection 104. As shown in FIG. 10, there are buttons for "Capture Video" 106, "Quiz" 108, "Sign", 110, and "Bypass Quiz" 112. There is also a "Save" button 114.

Figure 11:
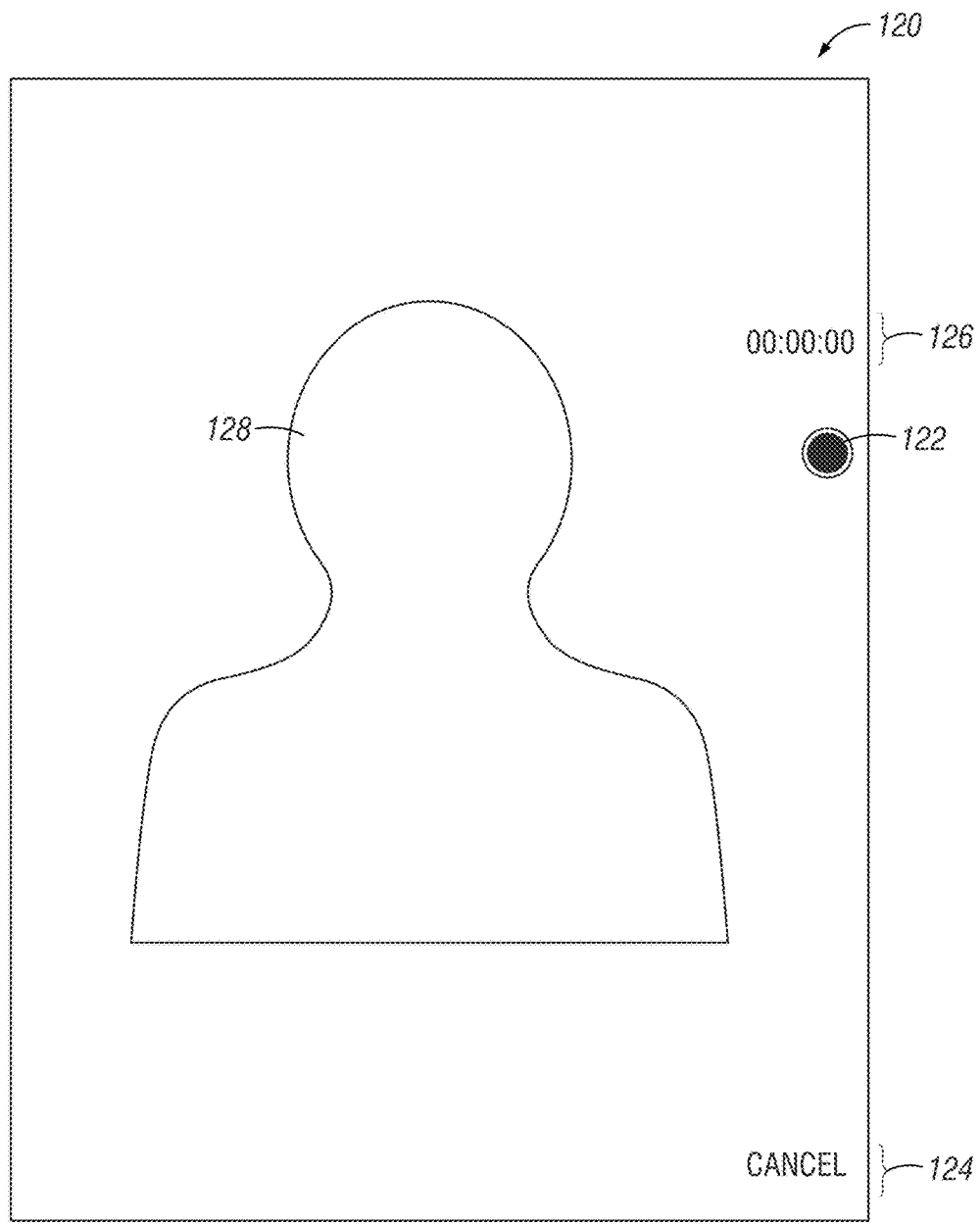
FIG. 11 is a screen display for a mobile app which displays video of a patient.

FIG. 11 is a screen display 120 for a mobile app which displays video of a health care provider 128. A timer 126 may be present as well as a record/stop button 122 and an option to "Cancel" 124. Thus, video of the health care provider may be recorded to assist in documenting the informed consent of the patient.

Figure 12:
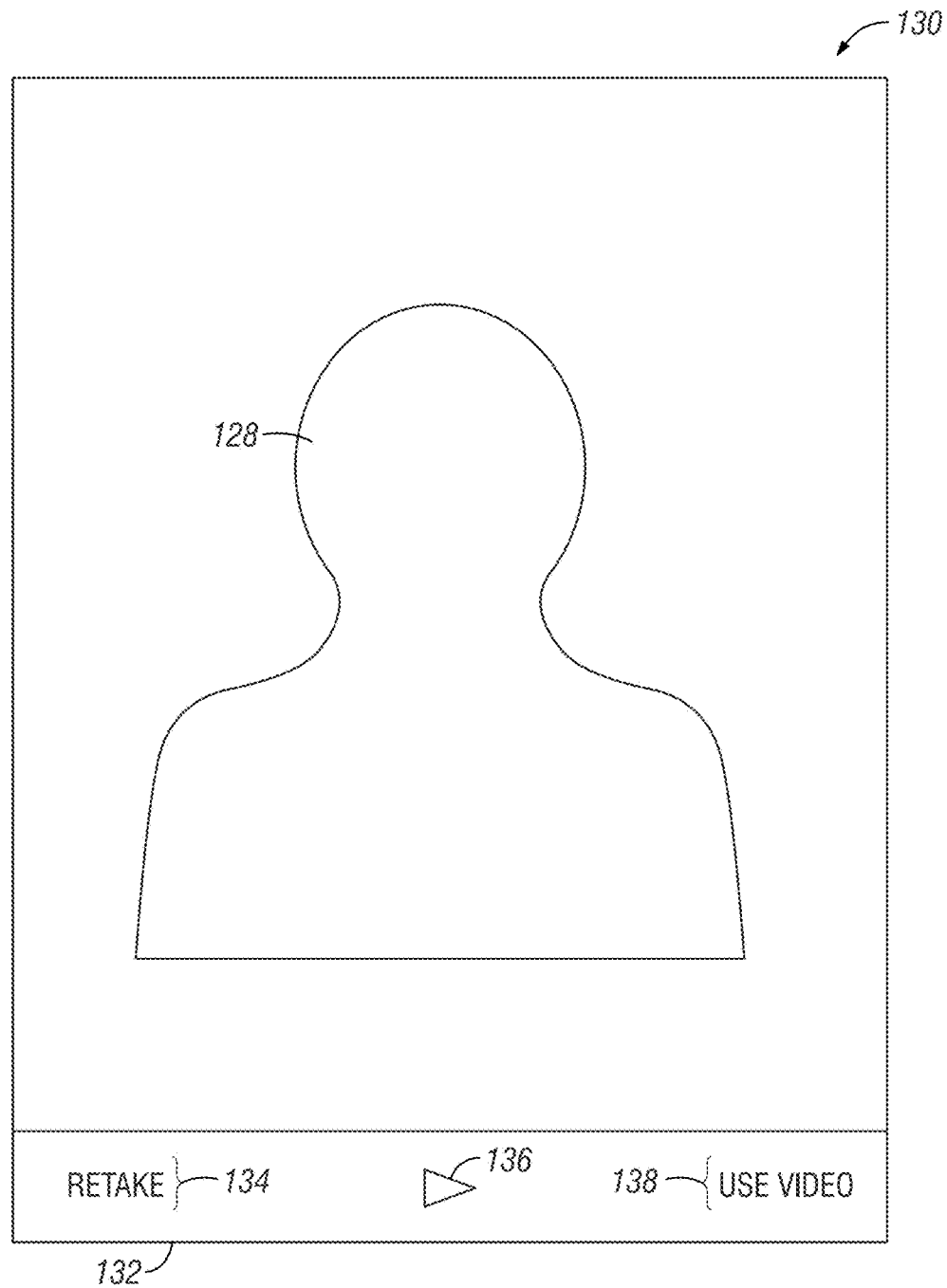
FIG. 12 is another screen display for a mobile app which displays video of a patient.

FIG. 12 is another screen display 130 for a mobile app which displays a video. The screen display 130 may be displayed after video has been recorded. User options are shown along the bottom of the screen display 130. The user may select "Retake" to retake the video if they are unsatisfied for any reason. A "play" button 137 is shown to play the video. If the user is content with the video then they may select to "Use Video" 138.

It is also contemplated that the mobile app may allow a video to be selected from a library of videos. The videos may be videos of the health care provider, colleagues of the health care provider, or others. Thus, for example, instead of the health care provider recording a video each time, the health care provider can select to display to the patient a pre-recorded video. It is contemplated that when a video is pre-recorded and will be used more than once that even greater thought can go into the presentation of the information to present information in the easiest to follow manner and a higher production quality may go into the video. It is also contemplated that particular videos may become accepted within the medical community as appropriate in particular instances. Alternatively, different videos may become accepted within particular hospital systems or physician groups as best practices. Similarly different videos may be endorsed by particular insurance companies, medical organizations, or others. It is contemplated that the videos may be included within the app, may be provided by the health care provider, or may be purchased through an in-app purchase or otherwise.

Figure 13:
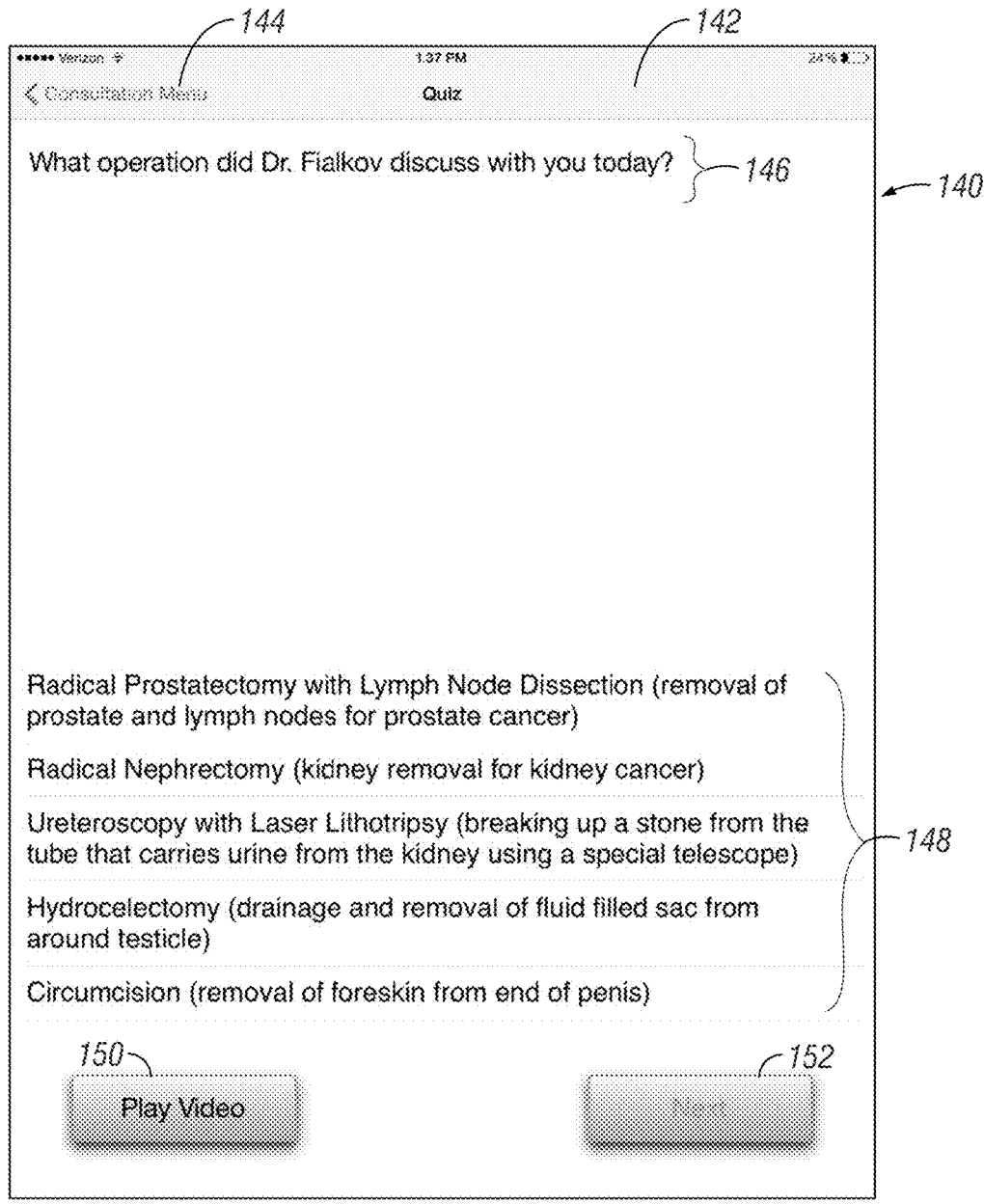
FIG. 13 is a screen display for a mobile app which presents a quiz.

FIG. 13 is a screen display 140 for a mobile app which presents a quiz. A menu bar 142 is provided that allows the "Consultation Menu" to be selected to return the user to a previous screen. The quiz includes a question 146. Multiple choice answers 148 are also shown. One example of a representative question is "What operation did Dr. Fialkov discuss with you today?" The answers include various examples of operations one of which was actually discussed. The user is also given the option of selecting a "Play Video" button 150. A "Next" button is also shown. The "Next" button may be disabled unless and until an answer is selected.

Figure 14:
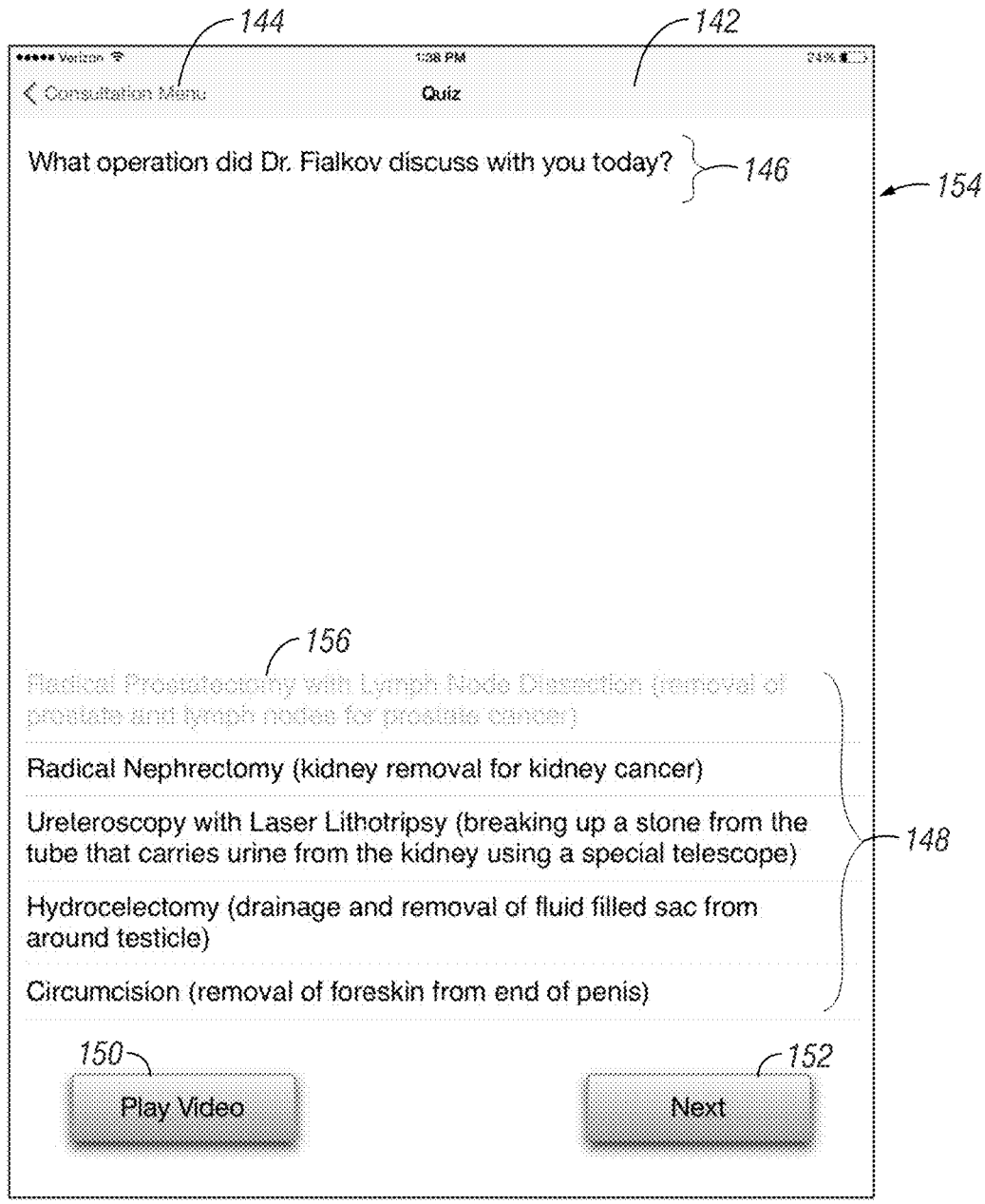
FIG. 14 is a screen display for a mobile app after a patient has selected an answer to a question of a quiz.

FIG. 14 is a screen display 154 for a mobile app after a patient has selected an answer to a question of a quiz, in this instance "Radical Prostatectomy with Lymph Node Dissection (removal of prostate and lymph nodes for prostate cancer)" 156. Here, the patient has selected the correct answer to the question.

Figure 15:
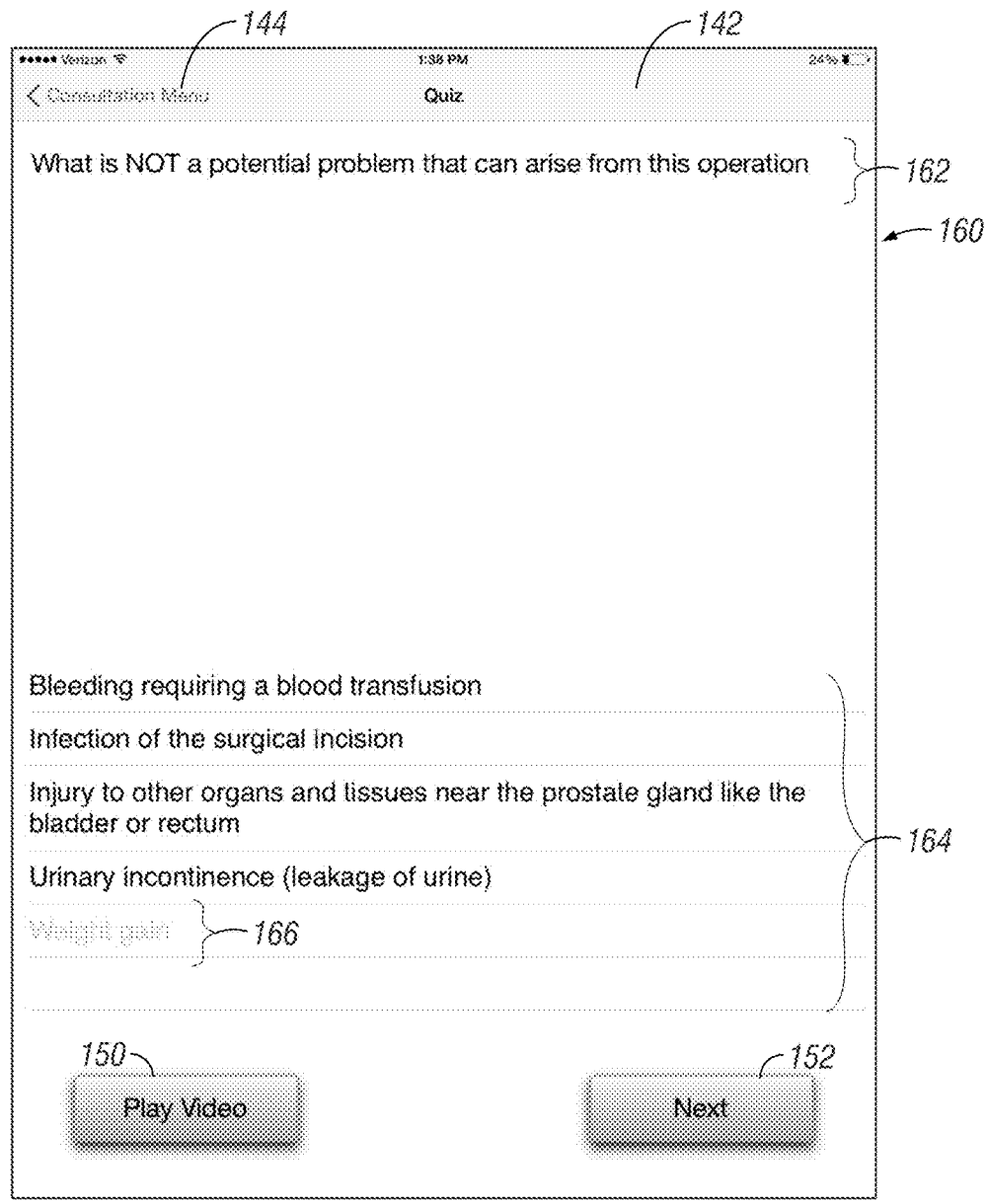
FIG. 15 is a screen display for a mobile app showing another example of a quiz question and an answer has been selected by a patient.

FIG. 15 is a screen display 160 for a mobile app showing another example of a quiz question and an answer has been selected by a patient. Here the question 162 is "What is NOT a potential problem that can arise from this operation?" Various answers 164 are provided. Here a patient has selected "Weight gain" 166 which is also a correct answer.

Figure 16:
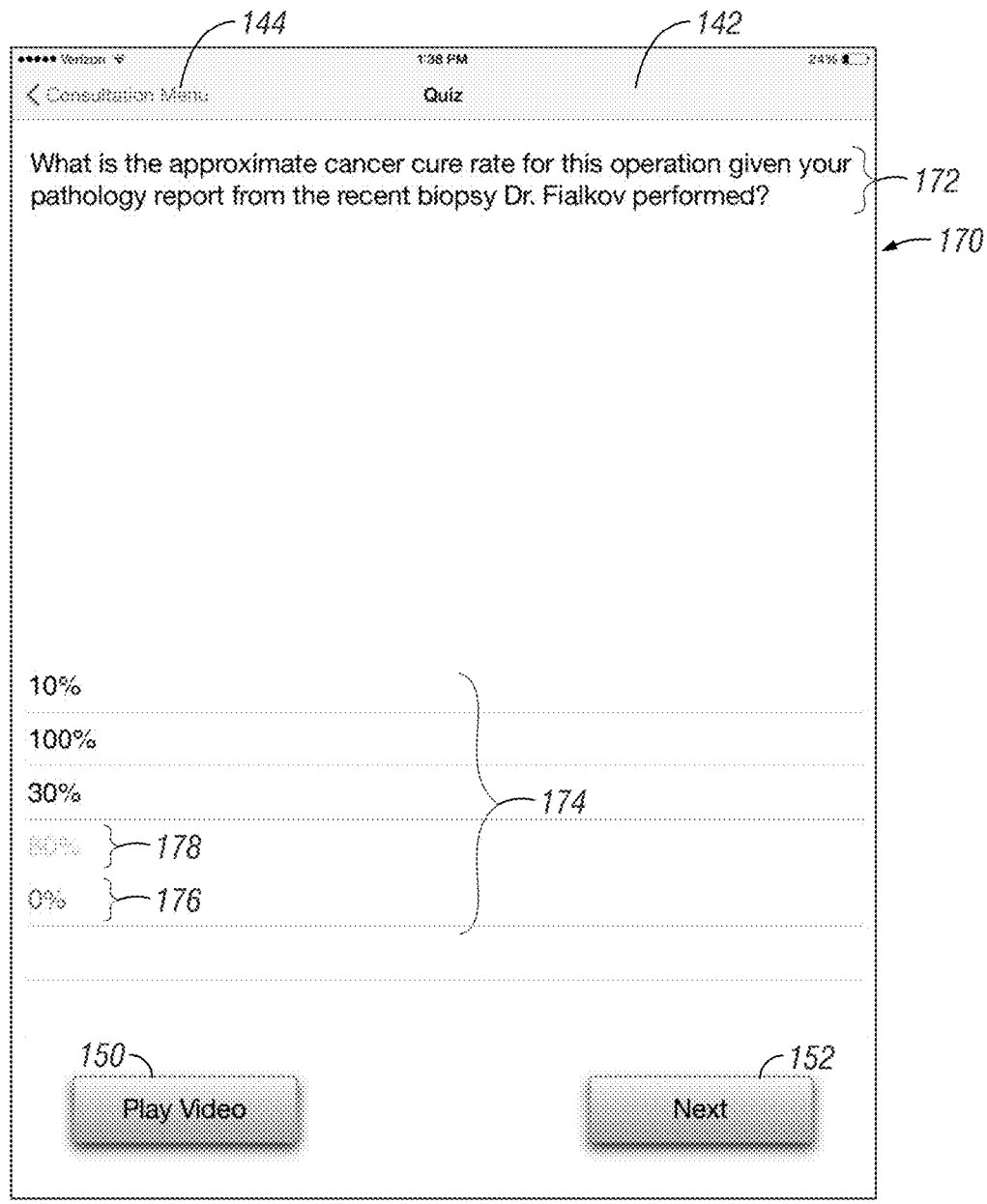
FIG. 16 is a screen display for a mobile app showing yet another example of a quiz question and an answer which has been selected by a patient.

FIG. 16 is a screen display 170 for a mobile app showing yet another example of a quiz question and an answer which has been selected by a patient. Here, the question 172 is "What is the approximate cancer cure rate for this operation given your pathology report from the recent biopsy Dr. Fialkov performed?" Various answers 174 are shown. A patient may select an incorrect answer 176 after which a correct answer 178 may be highlighted or emphasized in a different color. Thus, if the patient responds incorrectly, the patient is immediately informed of the correct answer. If the patient desires they can review the video again by selecting the "Play Video" button 150. Note that the patient may select the "Play Video" button before or after they answer.

Figure 17:
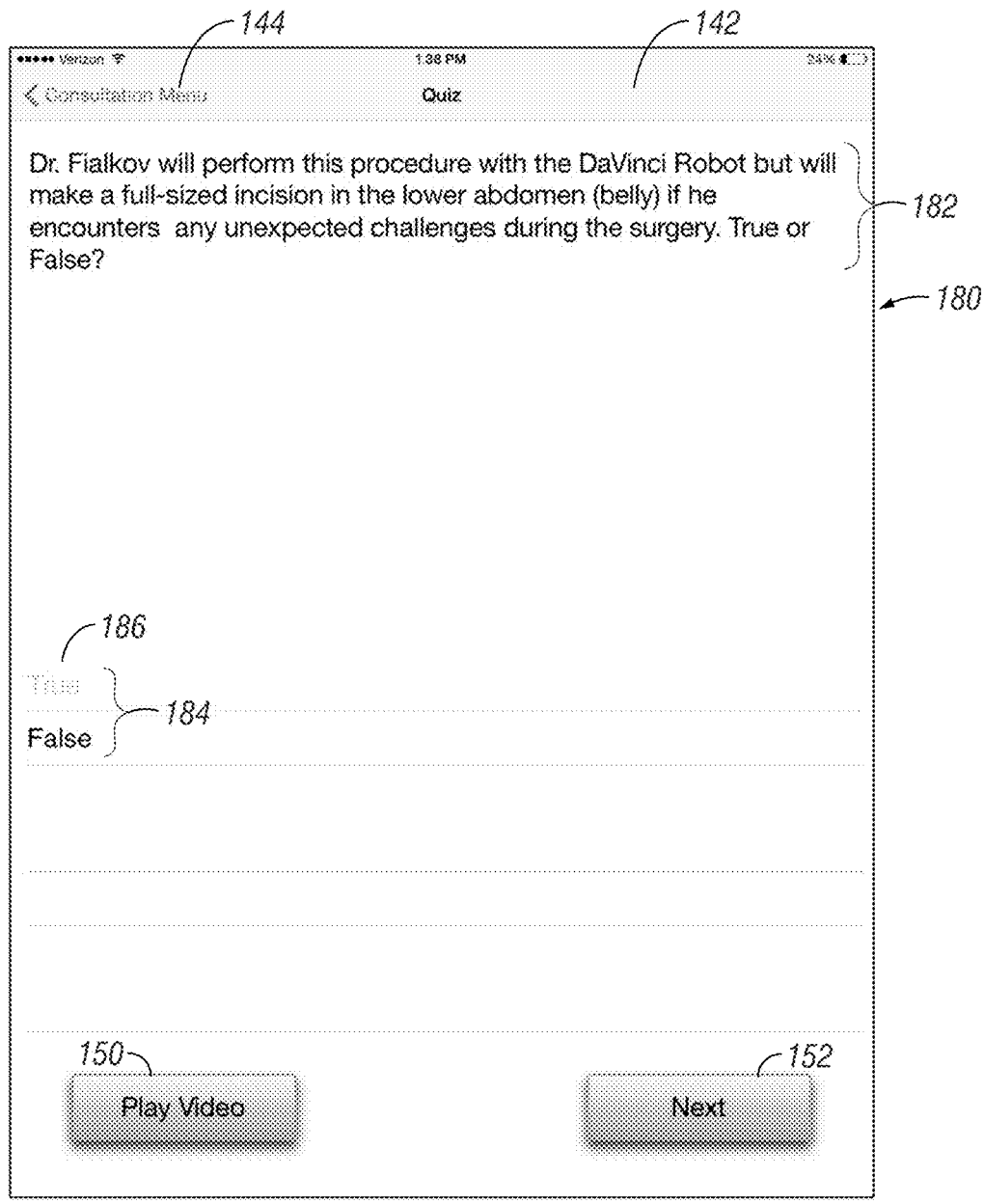
FIG. 17 is a screen display for a mobile app showing an example of a true/false question and answer to a quiz question.

FIG. 17 is a screen display 180 for a mobile app showing an example of a true/false question 182 and answers 184 to the quiz question 182. Here, the correct answer "True" 186 is selected by the patient.

Figure 18:
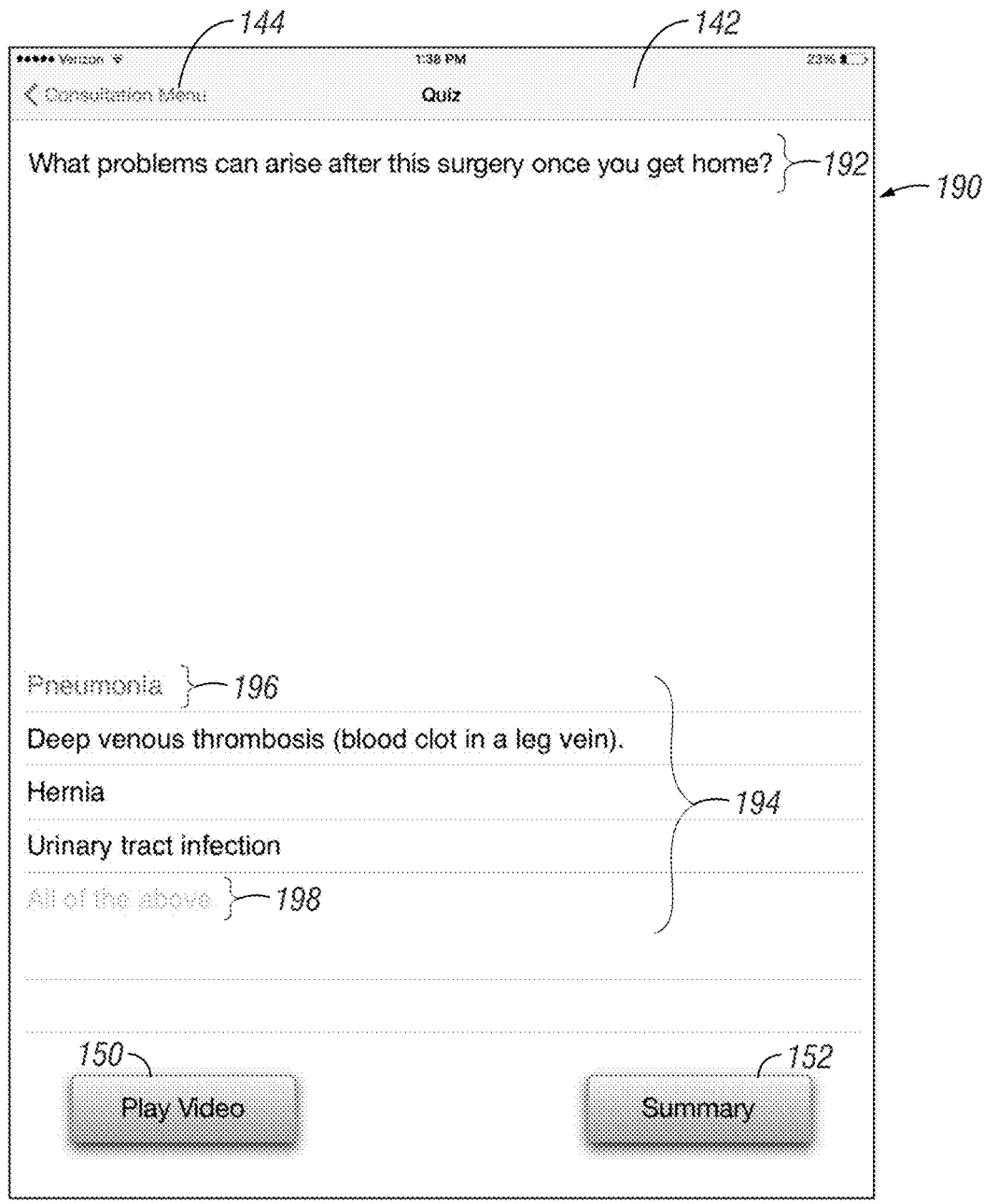
FIG. 18 is a screen display for a mobile app showing an example of a quiz question, a user's answer to the quiz question and a correct answer to the question.

FIG. 18 is a screen display 140 for a mobile app showing an example of a quiz question 192 and multiple choice answers 194. A user's answer 196 to the quiz question 192 is shown as well as the correct or best answer 198. Instead of a next button, a "Summary" button 152 is shown upon completion of the quiz.

FIG. 19 is a screen display 208 for a mobile app showing an example of quiz results 202. A user can return to the quiz by selecting "Quiz" 204. Each of the questions are shown again as well as the correct answer if the correct answer was selected by the patient. Where the patient did not select the correct answer the patient's selection is also shown. Thus, the patient is able to review all of the quiz questions and answers.

Figure 20:
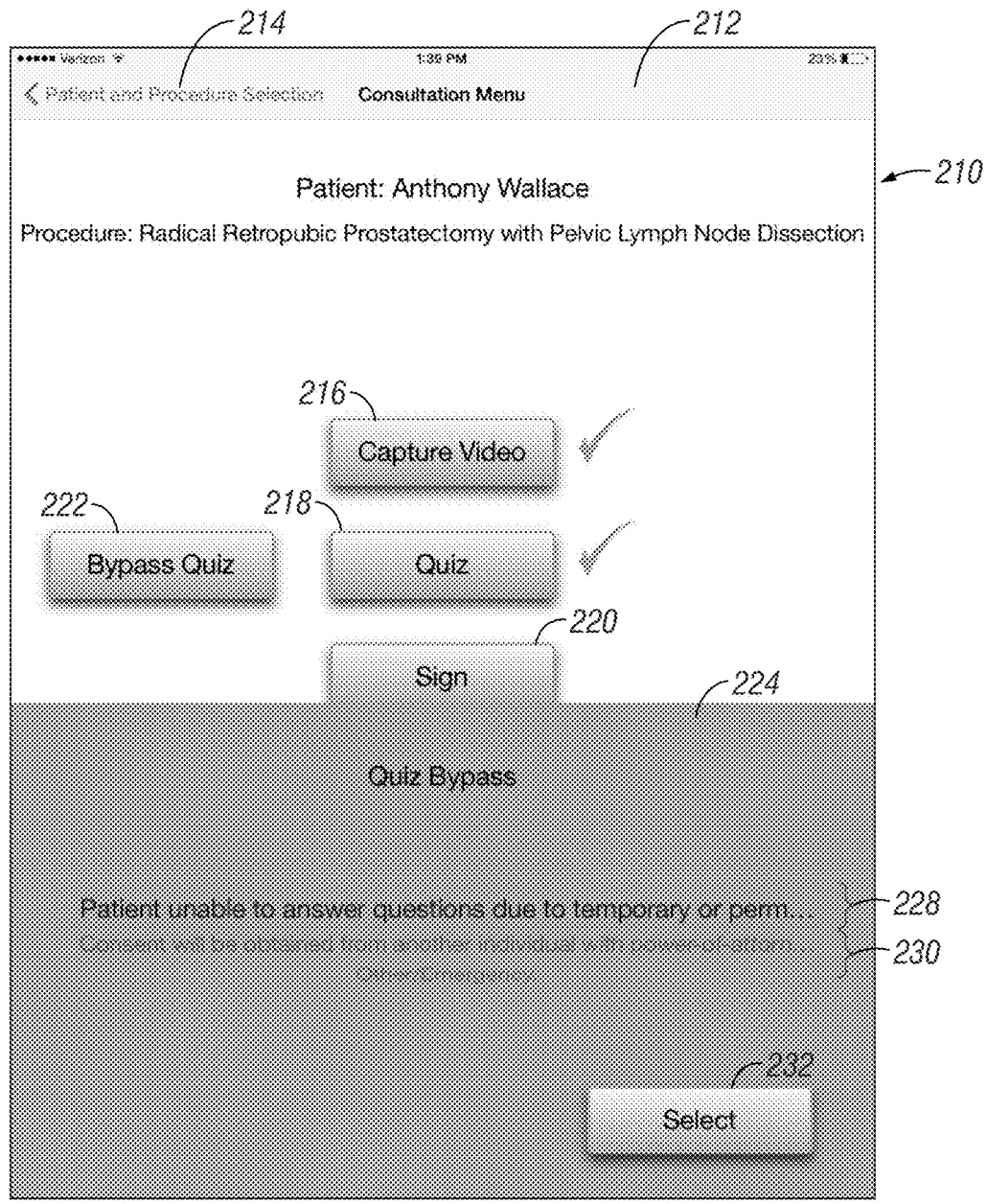
FIG. 20 is a screen display showing a mobile app with a consultation app where a user has selected to bypass the quiz.

FIG. 20 is a screen display 210 showing a mobile app with a consultation app where a user has selected to bypass the quiz. A quiz bypass area 224 is shown which allows a user to select a reason why the quiz is being bypassed. There may be various reasons why it may not be necessary or appropriate to implement the quiz such as the patient being unable to answer questions due to a temporary or permanent incapacity 228 or because consent will be obtained from another individual with power of attorney 230, it is an emergency situation, or other reason. Once the reason to bypass the quiz has been given the user may choose the "Select" button 232.

FIG. 21 is a screen display 240 showing a mobile app with a consent for surgery or procedure document 242. At the top of the screen display a user may select the Consultation Menu 246 to return to the previous screen or choose "Save" 244 to save the document after it has been signed.

Figure 22:
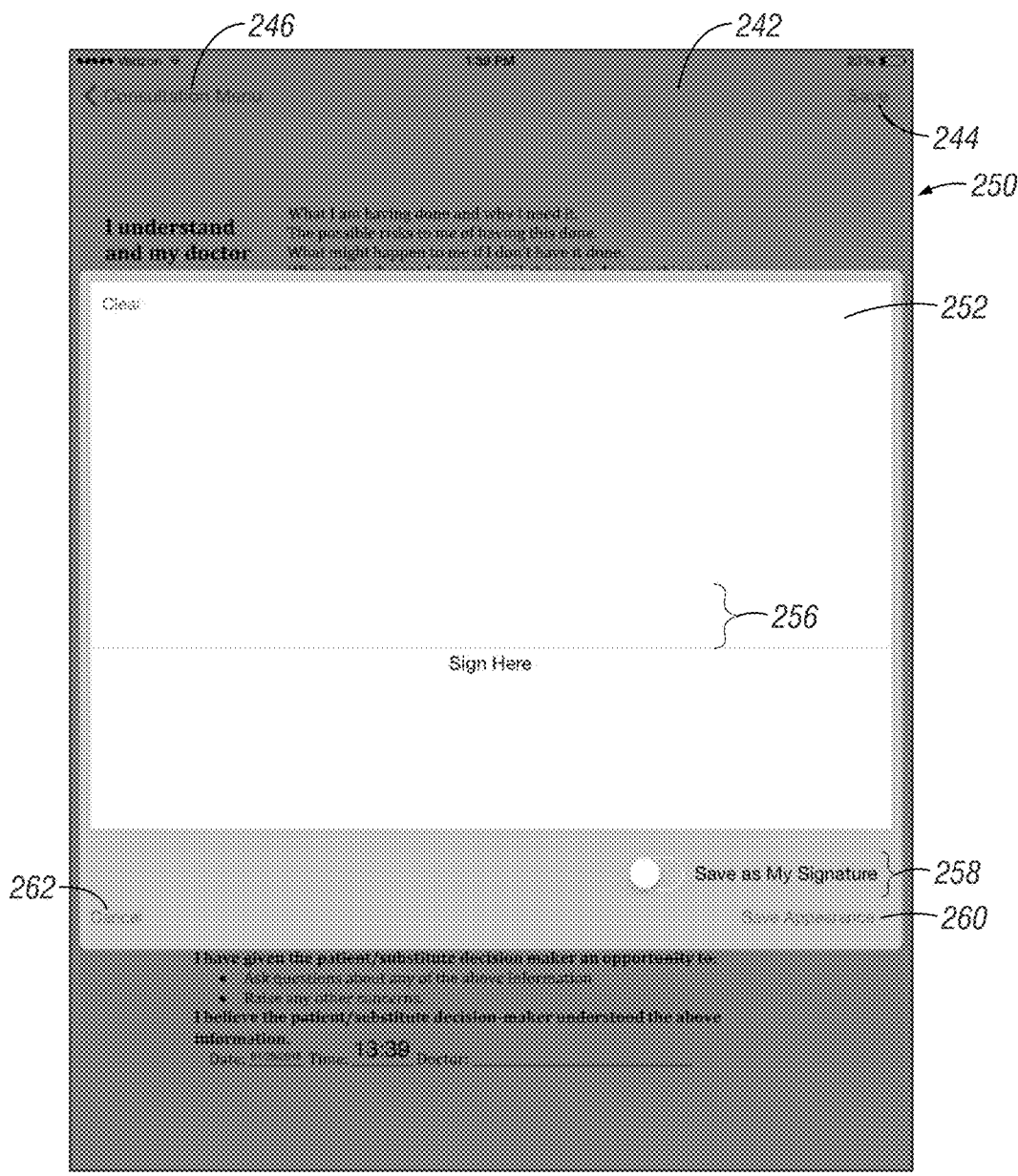
FIG. 22 is a screen display showing a mobile app which allows a patient to sign a consent document.

FIG. 22 is a screen display 250 showing a mobile app which allows a patient to sign a consent document. A signature area 252 is shown allowing a patient or other authorized individual to sign above the signature line 256. An option for saving the signature 258 is presented as well as an option to "Save Appearance". An option to "Cancel" 262 is also provided. Thus, after a patient has been informed about a procedure they can sign to indicate their consent.

Figure 23:
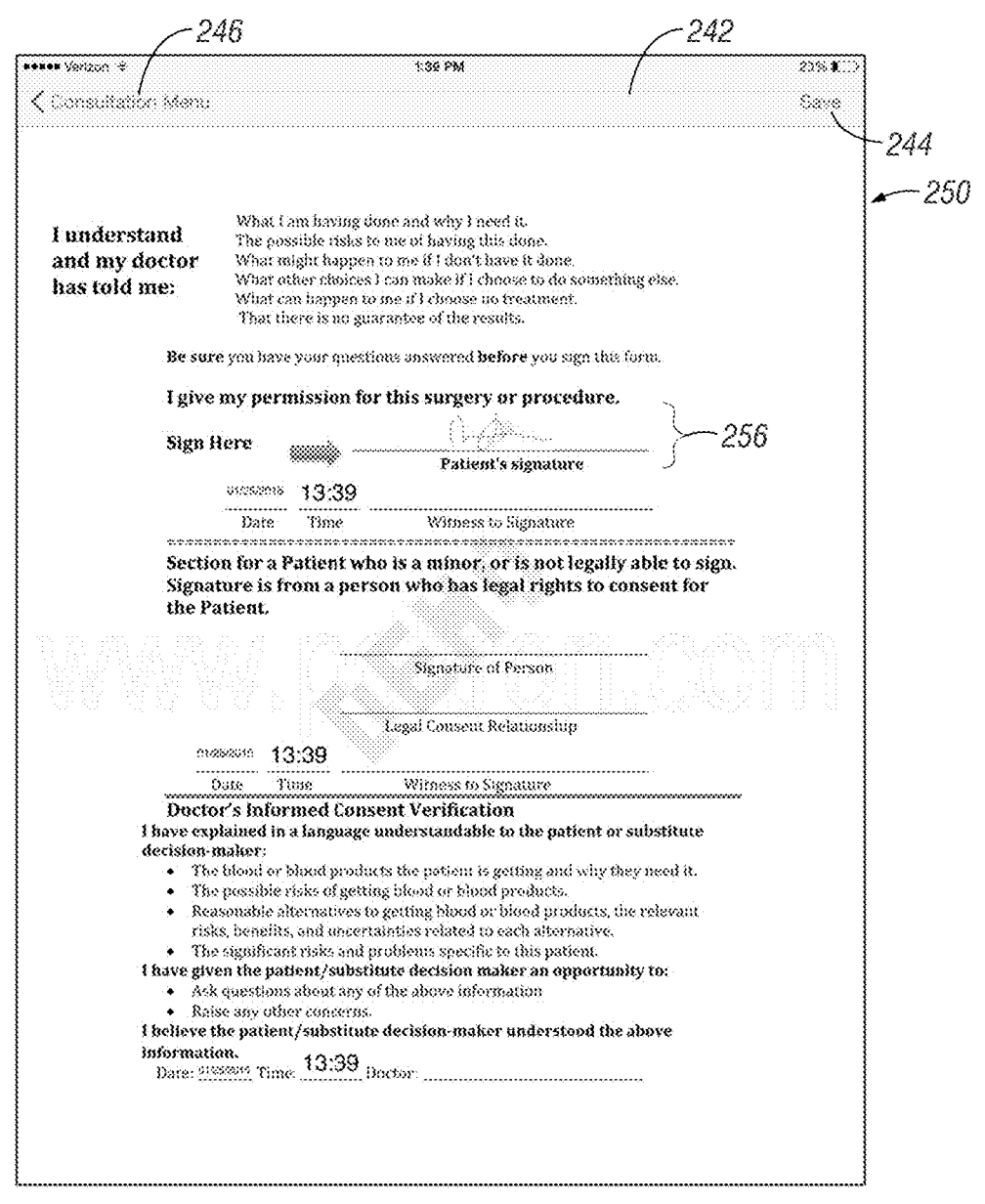

FIG. 23 illustrates the screen display 250 of FIG. 22 showing a mobile app with a signed consent document after a patient has provided their signature 256.

Figure 24:
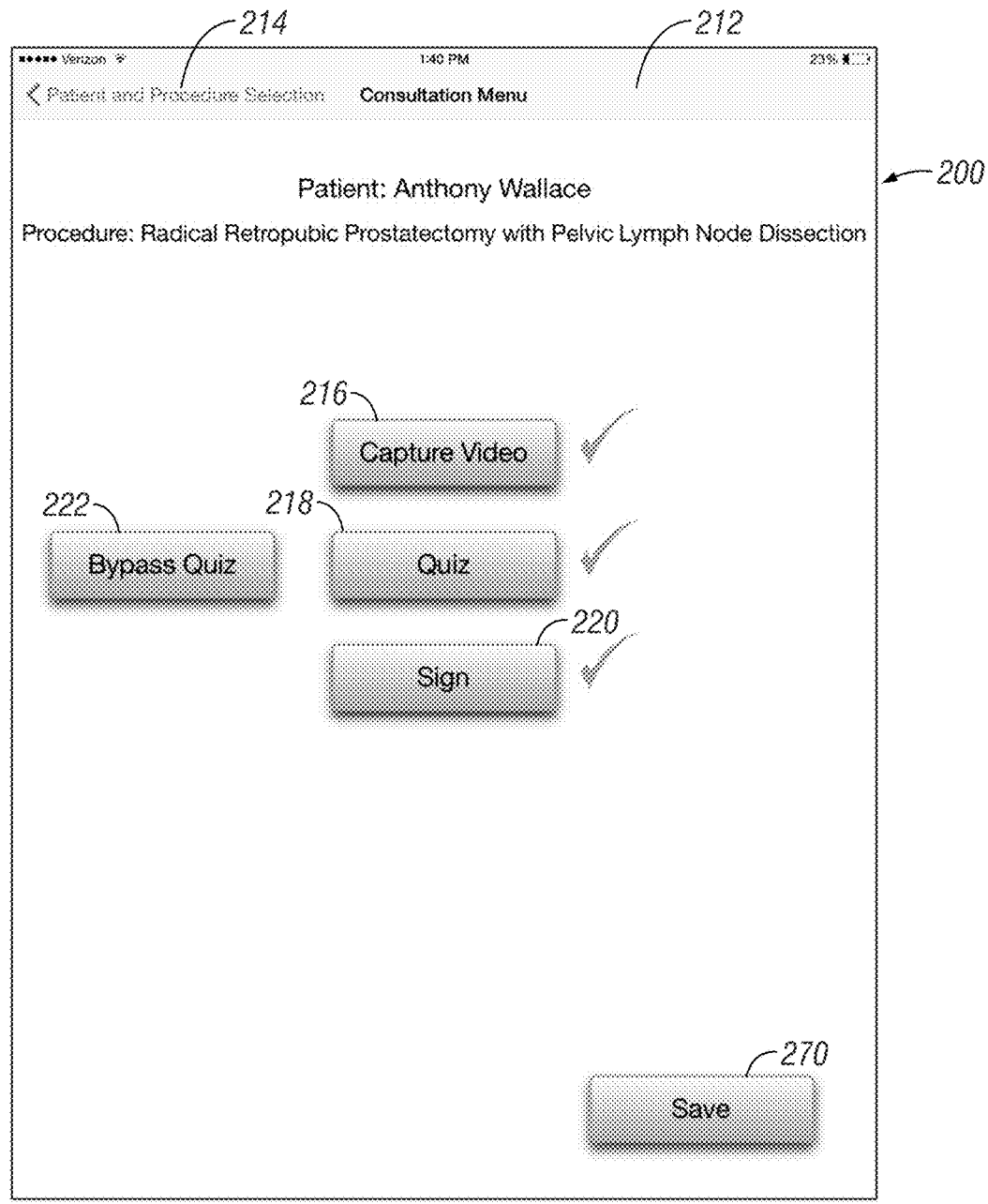
FIG. 24 is a screen display for a mobile app showing a patient, a procedure, and indicating that video has been captured, a quiz has been completed, and a signature has been provided.

FIG. 24 illustrates the screen display 200 for a mobile app showing a patient and a consultation menu 212. As shown in FIG. 24, there are checkmarks to indicate that different steps have been performed. In particular, it is clear that video has been captured, the quiz has been completed, and a signature has been provided. The "Save" button 270 can be selected to save the information associated with the procedure.

Figure 25:
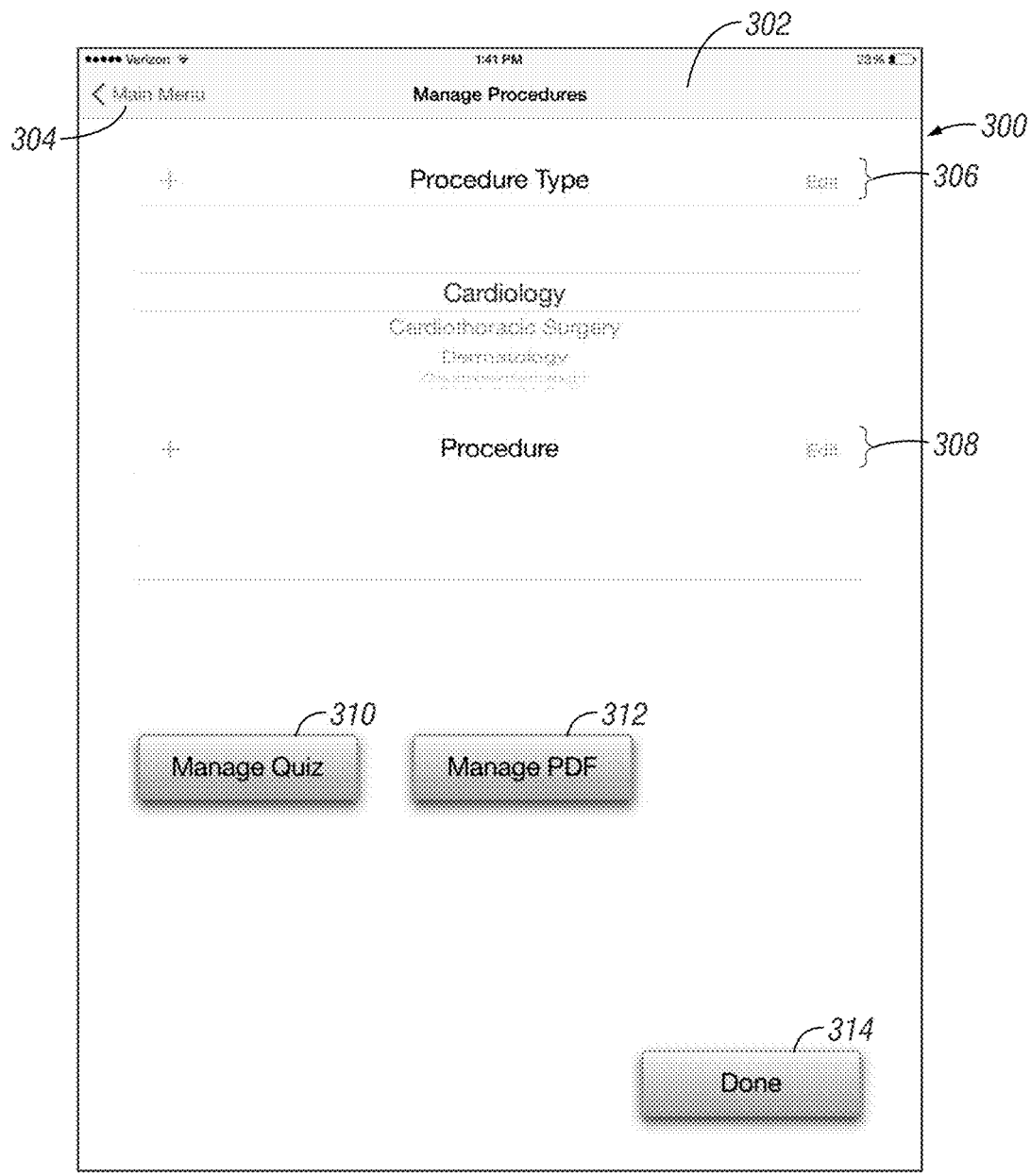
FIG. 25 is a screen display for a mobile app showing a manage procedure screen.

FIG. 25 is a screen display 300 for a mobile app showing a manage procedure screen. This allows a health care provider using the mobile app to setup different types of procedures by selecting to "Edit" 306 procedure types and "Edit" 308 different procedure types. There is a "Manage Quiz" button 310 and a "Manage PDF" button 312. A "Done" button 314 is also shown.

Figure 26:
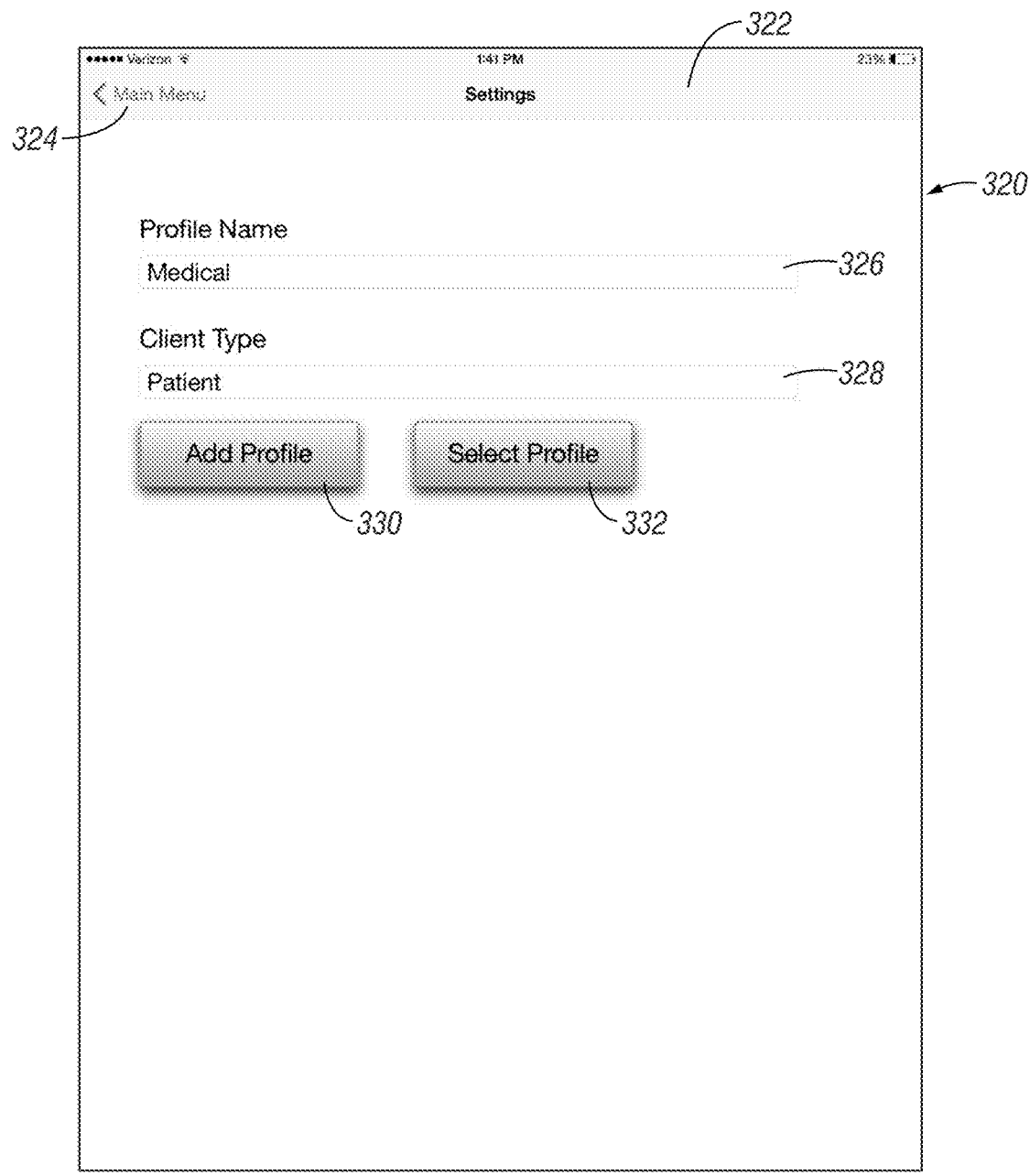
FIG. 26 is a screen display for a mobile app showing a settings screen.

FIG. 26 is a screen display 320 for a mobile app showing a settings 322 screen. A user may select "Main Menu" 324 to return to the main menu if the user chooses to do so.

The user is allowed to enter a profile name 326 and a client type 328. The user can select to "Add Profile" 330 or "Select Profile" 332.

Figure 27:
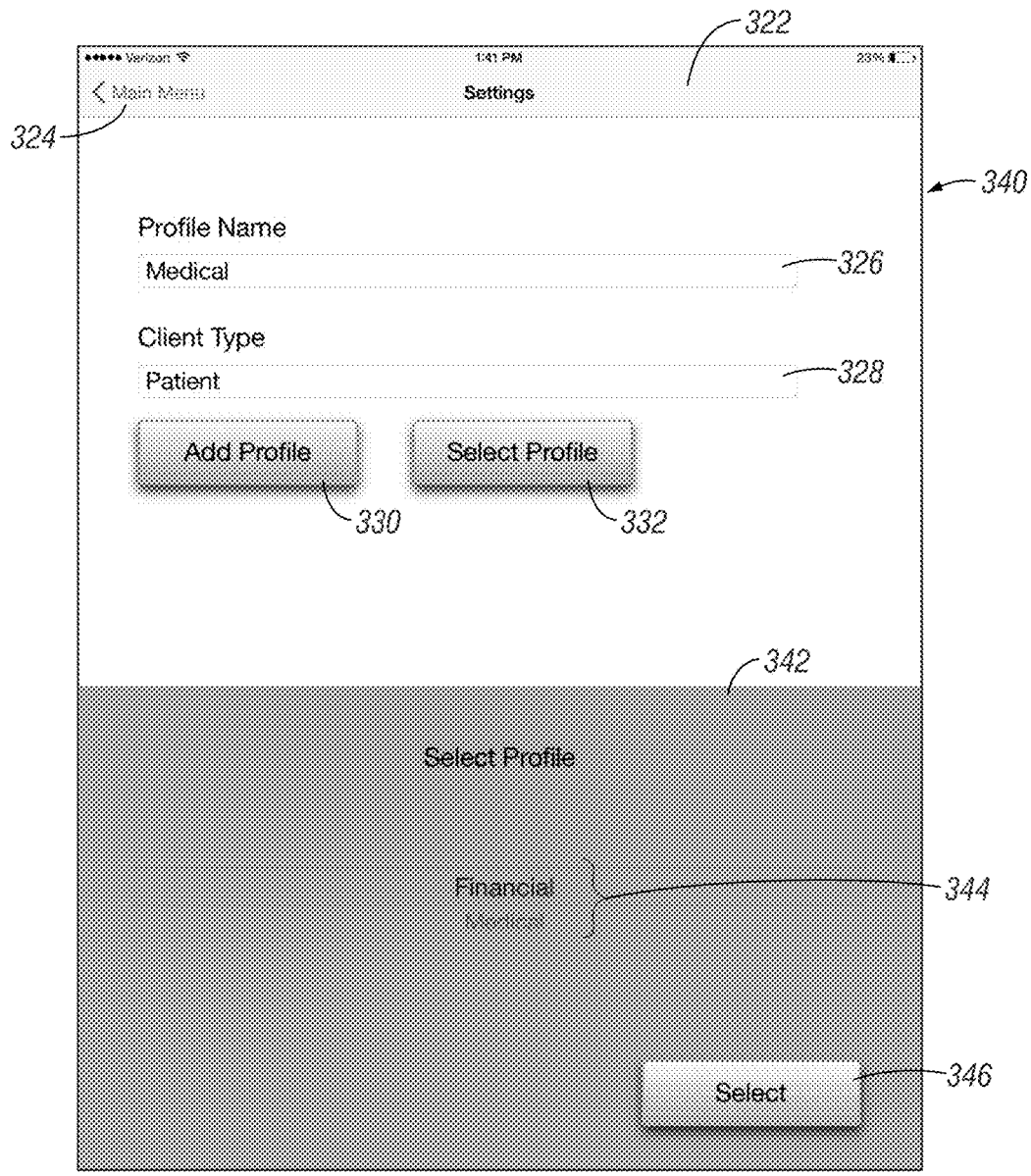
FIG. 27 is a screen display for a mobile app showing a settings screen where a profile is selected.

FIG. 27 is a screen display 340 for a mobile app showing a settings screen where a profile is selected. Here an area 342 is shown with a set of profiles 344 from which the user can select. Thus, the app can be configured for different uses such as financial, medical, legal, etc. There are numerous examples of situations where informed consent is important and/or where one party has a duty or obligation to obtain informed consent from another party.

Figure 28:
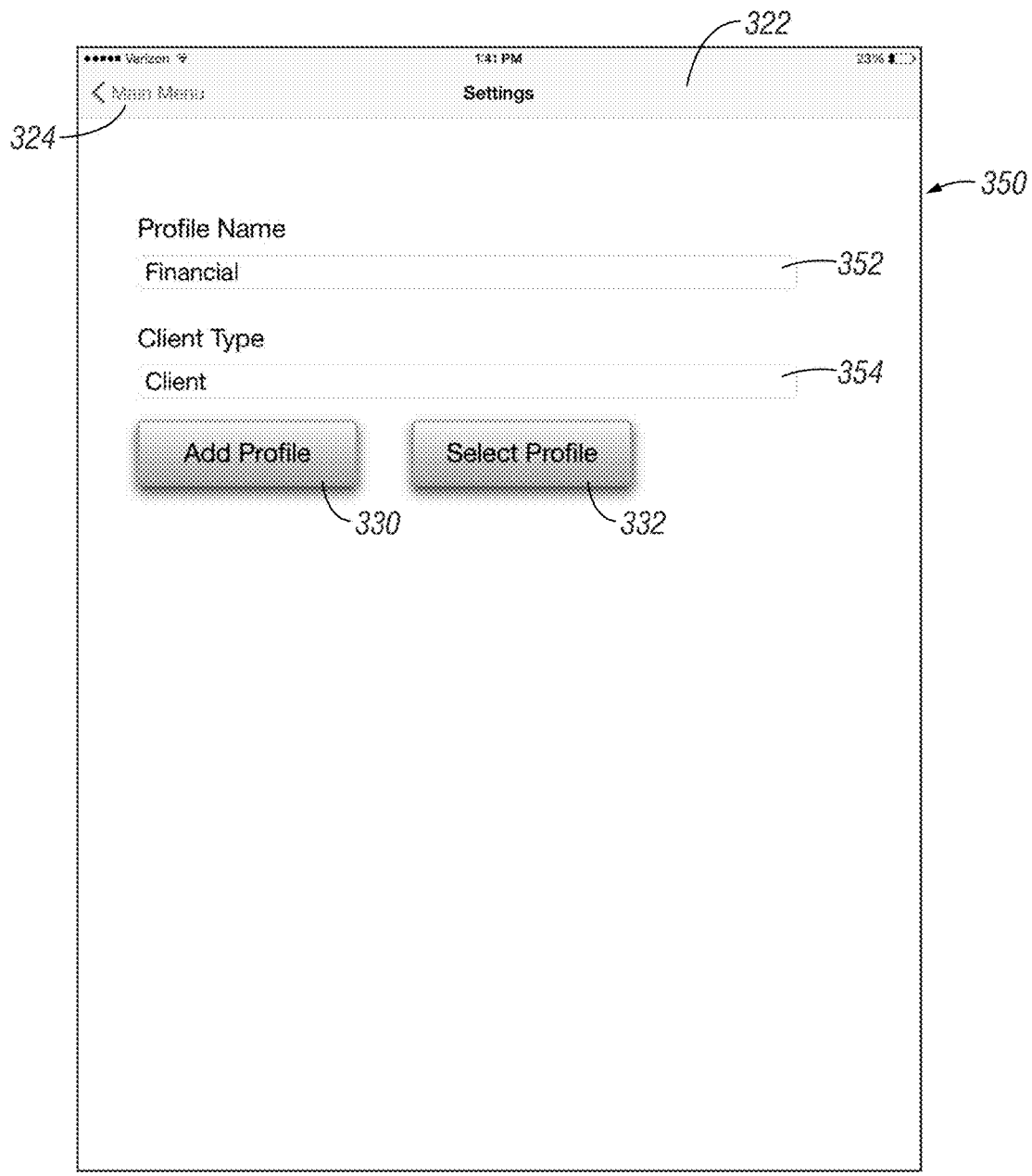
FIG. 28 is another example of a screen display for a mobile app showing a settings screen.

FIG. 28 is another example of a screen display 350 for a mobile app showing a settings screen. Note that in FIG. 28 the profile name shown is "Financial" 352.

Figure 29:
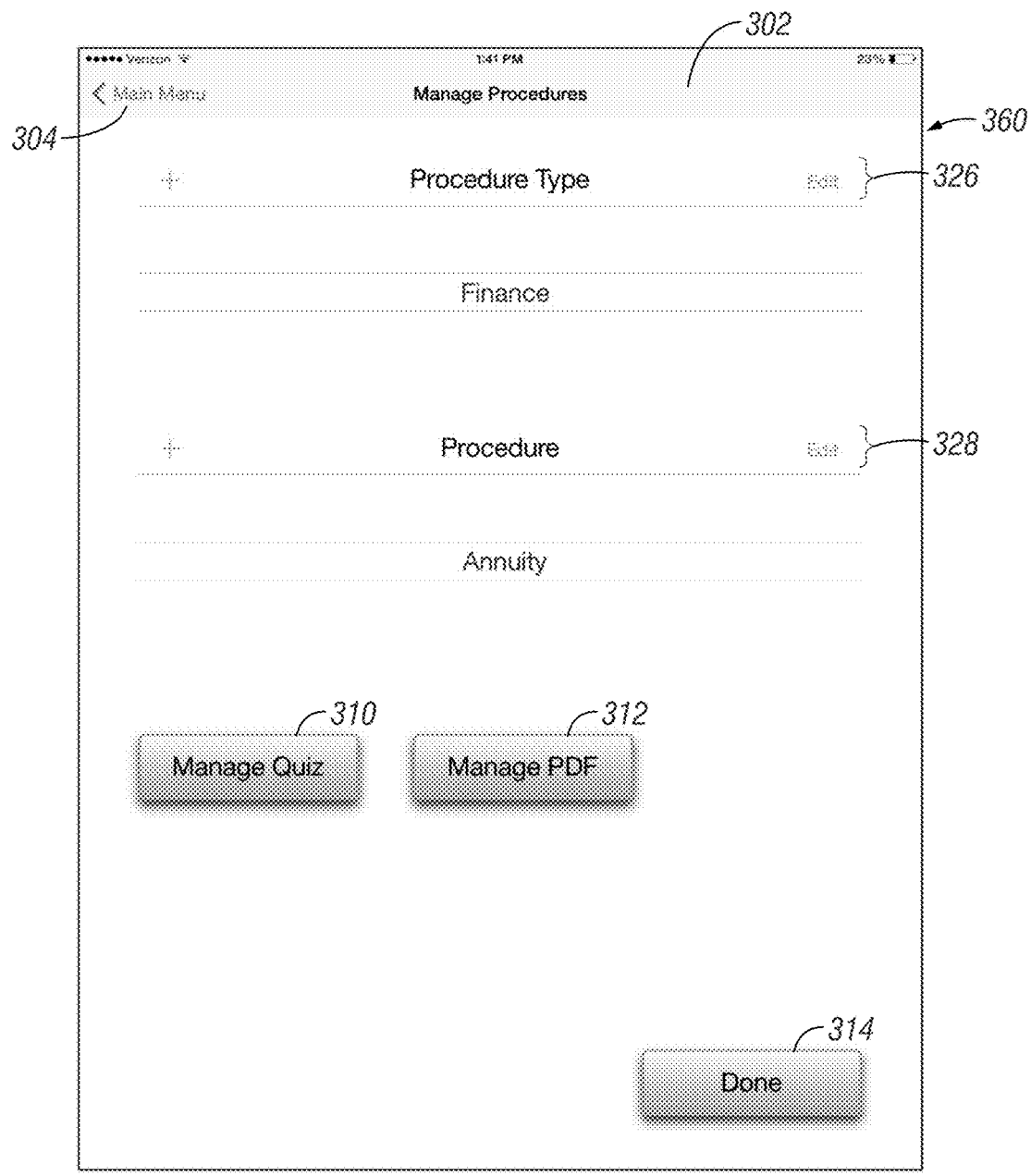
FIG. 29 is a screen display to manage procedures.

FIG. 29 is a screen display 360 for managing procedures. Here the type of procedure is "Finance" and the procedure is "Annuity." Thus, there are many possible uses for the informed consent applications which may be used in financial, legal, medical, or other situations.

It should be understood that a number of features may be incorporated into the mobile app to ensure privacy and security. For example, it is contemplated that a patient using a computing device with the app to take the quiz, for example, would not be able to see the screen which would allow them to see the names of other patients. This can be accomplished by requiring the health care provider's password to view such a screen or otherwise locking the patient out from those portions of the app which they are not permitted to view.

It should also be understood that video is preferably not stored on the computing device at all or if so, only temporarily. Instead, video is streamed to a server for storage or alternatively video may be temporarily saved on the computing device for purposes of uploading to the server and then deleted or wiped from the computing device so that no version of the video remains on the computing device. Other patient data may be similarly treated including consent documents and quiz results.

Although discussed primarily with respect to informed consent, it is noted that the use of the video cameras in the examination rooms can be used for other purposes related to documenting patient encounters. For example, health care providers are often subjected to false accusations. Accusations of any sort are taken very seriously and investigated thoroughly which can be time consuming for investigators as well as the health care provider involved. Moreover, even unsubstantiated allegations and the mere fact that an investigation took place can have a negative effect on the careers of health care providers. Such accusations can include accusations of sexual assault. One way such accusations can be guarded against is to have a female nurse or other staff member present during a male physician's examination of a female patient. However, this unnecessarily uses resources. Having a video camera present makes a record of the encounter which could be used not only to address false accusations of assault or other wrongdoing but to conclusively prove it unfounded and to use as evidence against the false accuser in criminal or civil litigation. Mere knowledge of the use of the video cameras may provide a significant deterrent to false accusations.

This documentation could be used for other purposes including addressing insurance disputes regarding whether procedures occurred and/or the level of care provided (e.g. the diagnosis codes used to support a particular intervention). Thus, it is to be understood that the video system described may be used for purposes other than informed consent.

Although various methods and systems have been described herein, it is to be understood that the present invention is not to be limited to the specific embodiments described. Moreover, the present invention contemplates numerous variations, additions, modifications, options, and alternatives.

A few examples of options and alternatives for the aspects of an informed consent system such as above described will follow.

Figure 30:
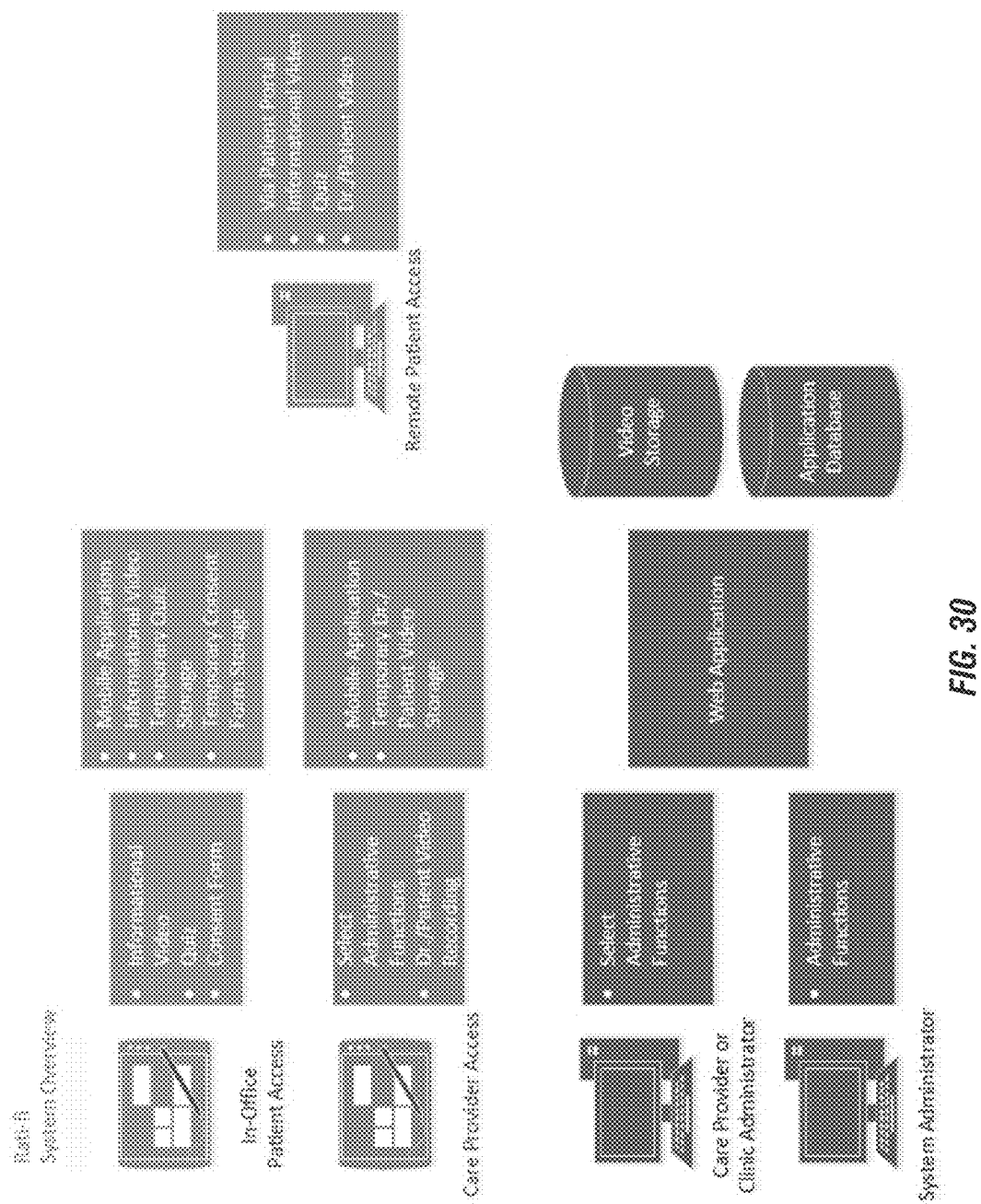
FIG. 30 is a schematic diagram of an integrated system such as could be used for informed consent at different times and for different events in a patient, health care provider context.

With reference to FIG. 30, the ability to have an integrated, wide-ranging system is illustrated. Both direct patient/health care provider interactions and/or remote patient/health care provider interactions are possible, including utilization of the techniques and aspects described above. This can include automatically providing content to assist in the "informed" side of "informed consent". Examples are through informational videos or other content. Further examples are the presentation of quizzes or testing for understanding of that content.

FIG. 30 also shows how documentation can occur, an important aspect to many informed consent scenarios.

FIG. 30 also illustrates how an overall system could be implemented. Use of servers or computers in different capacities and locations, as well as web application, mobile applications and the like are shown.

Figure 31:
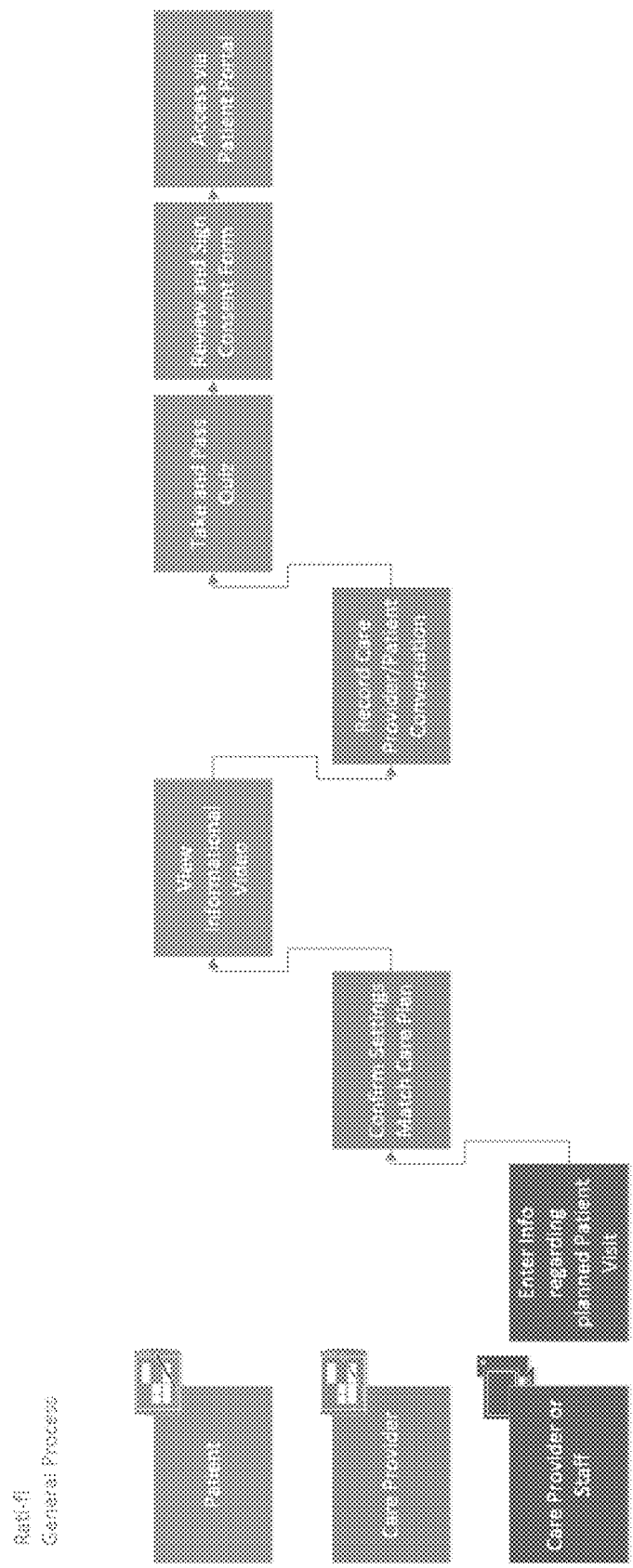
FIG. 31 is a block diagram of one example of a flow process in the context of a patient/health care provider informed consent process.

FIG. 31 shows one example of a process flow for a patient/health care provider informed consent implementation. The flow process includes the initial entering of information regarding the visit. There can be a match of existing or entered information relative a care plan established for the patient. The flow chart includes the presentation (in some form) to the patient of in this example an informational video regarding proposed procedure or treatment. In this example, a recording (audio, video, audio and video, as examples) can be taken of the health care provider/patient conversation after the informational video. The patient then takes a quiz until verification of a passing level. The patient reviews and signs a consent form. That captured and stored form consent is then made available to relevant parties via access to the patient portal. This can be the patient, the health care provider, or another authorized person.

As can be appreciated by those skilled in the art, the platform in which the invention and its aspects can be delivered can vary according to need or desire. Below is one example for a web application version. C no. ASP.NET web API with Azure SQL backend and data storage; encrypted Azure datastore for the video consultations and pdfs (or similar) for transmitting documents and content; Angular JS and Bootstrap UI for a website interface; and Microsoft Azure for the hosting (a HIPAA compliant platform). As can be appreciated, variations obvious to those skilled in the art are possible.

Figure 32:
FIG. 32 is one example of a verification technique for confirming understanding of content to a high level of competence such as could be used with the present system.

A further optional feature would be to add additional techniques for gaining a high level of confidence of understanding by the patient or other person from which informed consent is sought of the educational content provided before requesting consent. One example is as follows. A PEMAT-A/V (Patient Education Materials Assessment Tool for Audio Visual materials) is an example of a scoring system that gives a high level of competence of understandability and actionability for content (such as the educational videos) contemplated with the present embodiments. FIG. 32 is an example of such a technique. The PEMAT-A/V assessment tool is defined as a systematic method to evaluate and compare the understandability and actionability of patient education materials. See http://www.ahrq.gov/professionals/prevention-chronic-care/improve/self-mgmt/pemat/pemat1.html (accessed online Aug. 19, 2015) which is incorporated by reference herein. Understandability is defined as patient education materials "when consumers of diverse backgrounds in varying levels of health literacy can process and explain key messages"; actionability is defined "when consumers of diverse backgrounds and varying levels of health literacy can identify what they can do based on the information presented." Each of the educational videos contemplated in some of the embodiments could be reviewed by such a procedure for higher level of competence of understandability and actionability. Of course, other techniques are possible. FIG. 32 gives an idea of some of the techniques used in PEMAT-A/V for the indicated medical procedure in FIG. 32.

As will be appreciated in the art, an integrated system can have a variety of ancillary features. Below are examples.

The informed consent methodologies described above can be applied at various time points, milestones, or events in a context using informed consent. For example, some of the above examples relate to pre-operation counseling. Using the same infrastructure, including the stored video collection and patient registration through the web portal, the system could send text messages and emails to patients with links to post-operative education videos and pdf documents. The current development in health care is the use of patient satisfaction surveys by groups such as Press Ganey. Links could be added to the web-based patient satisfaction survey in the same text or email, or at a later date. A comprehensive system for educating patients, obtaining informed consent preoperatively, documenting the informed consent using time stamps, video and the GPS capability of a digital device (e.g., iPad) and providing post-op care instructions and patient satisfaction feedback are possible from the single platform.

As can be further appreciated by those skilled in the art, the informed consent can be applied in contexts beyond medical operations treatments. Some examples are with OSHA (Occupational Safety and Health Administration)-related contexts. For example, some safety workers need to be documented as understanding certain content. In an analogous way, embodiments could be configured to take worker information, present educational content regarding topic related to safety or an OSHA regulation, get high level confidence of understanding and actionability, and then get a signed form documenting the same.

In another example, workers in jobs with known risks could be required to give informed consent. Documenting the same with these techniques could then be put in the worker's file or the company's file. They would then be available for access if, for example, a workman's compensation claim was filed.

What is claimed:

1. A method for obtaining and documenting informed consent, the method comprising:

providing a software application to a computing device for executing on the computing device, wherein the software application is a mobile app and wherein the computing device is a mobile computing device, further comprising receiving through the software application information identifying a plurality of procedures and one or more procedure types;

receiving a selection of an individual into the software application executing on the computing device;

receiving a selection of a procedure for which informed consent is desired into the software application executing on the computing device wherein the procedure is a medical procedure and wherein the individual is a patient;

displaying an educational video to the individual using the software application executing on the computing device, the educational video containing educational content about the procedure for which the informed consent is desired further comprising receiving a selection of the educational video from a library of educational videos;

capturing video evidencing the informed consent for the procedure using the software application executing on the computing device;

making available a quiz for the individual using the software application executing on the computing device, the quiz including a plurality of questions about the procedure for assessing the informed consent further comprising receiving through the software application the plurality of questions about the procedure;

documenting administration of the quiz to the individual using the software application executing on the computing device;

presenting a document for signature to the individual using the software application executing on the computing device, the documenting indicative of the informed consent for the procedure further comprising receiving through the software application the document associated with the procedure;

receiving a signature on the document from the individual using the software application executing on the computing device; and sending to a server from the computing device the video, the document with the signature, and storing the video in a non-transitory computer readable data storage medium associated with the server to thereby provide for documenting the informed consent of the individual for the procedure wherein the video includes video of the patient acknowledging that they are providing informed consent and wherein the video includes video of the individual and a service provider interacting with the individual;

making the video available to the individual through a portal associated with the server and to a service provider of the individual through a portal associated with the server.

2. The method of claim 1 wherein the capturing video is performing using a camera integrated into the computing device.

3. The method of claim 1 further comprising receiving a selection of an option to bypass the quiz and documenting a reason for bypassing the quiz by sending the reason to the server.

4. The method of claim 1 further comprising purchasing the educational video through the software application.

\* \* \* \* \*